US012676223B2

(12) United States Patent
Coyne, III et al.

(10) Patent No.: US 12,676,223 B2

(45) Date of Patent: Jul. 7, 2026

(54) MEDICATION CONTAINER WITH APPLET-BASED DRUG DELIVERY PARAMETER CONFIGURATION

(71) Applicant: SHL Medical AG, Zug (CH)

(72) Inventors: Martin Michael Coyne, III, Towaco, NJ (US); Christopher James Franzese, Randolph, NJ (US); Mason Mitchell Watts, Owings Mills, MD (US); Stephen Allison Porter, Baltimore, MD (US); Mariano Mumpower, Baltimore, MD (US)

(73) Assignee: SHL Medical AG, Zug (CH)

( * ) Notice: Subject to any disclaimer, the term of this patent is extended or adjusted under 35 U.S.C. 154(b) by 0 days.

(21) Appl. No.: 19/083,966

(22) Filed: Mar. 19, 2025

(65) Prior Publication Data

US 2026/0106013 A1     Apr. 16, 2026

Related U.S. Application Data

(60) Provisional application No. 63/707,772, filed on Oct. 16, 2024.

(51) Int. Cl.
| | |
|---|---|
| *G16H 20/13* | (2018.01) |
| *A61J 1/18* | (2023.01) |
| *G06K 19/06* | (2006.01) |
| *G06K 19/07* | (2006.01) |

(52) U.S. Cl.
CPC ............... *G16H 20/13* (2018.01); *A61J 1/18* (2013.01); *G06K 19/06037* (2013.01); *G06K 19/0723* (2013.01); *A61J 2205/60* (2013.01)

(58) Field of Classification Search
CPC ...... G16H 20/13; A61J 1/18; G06K 19/06037
USPC ......................................................... 235/375
See application file for complete search history.

(56) References Cited

U.S. PATENT DOCUMENTS

| | | | | |
|---|---|---|---|---|
| 8,745,906 | B2 | 6/2014 | Cloninger | |
| 11,961,599 | B2 | 4/2024 | Blum | |
| 2013/0037616 | A1* | 2/2013 | Howell | G06K 19/02 |
| | | | | 235/492 |
| 2014/0052537 | A1* | 2/2014 | Garnet | G08G 1/133 |
| | | | | 705/14.63 |

(Continued)

FOREIGN PATENT DOCUMENTS

| | | |
|---|---|---|
| CN | 117954125 A | 4/2024 |
| EP | 2064663 B1 | 1/2011 |
| JP | 5939869 B2 | 6/2016 |

*Primary Examiner* — Allyson N Trail

(74) *Attorney, Agent, or Firm* — McDonnell Boehnen Hulbert & Berghoff LLP

(57)     ABSTRACT

The present disclosure provides a method for configuring a medicament container. The method includes filling a medicament container with a predetermined amount of a medicament, or obtaining a pre-filled medicament container. The method further includes obtaining, by a mobile terminal, a plurality of parameters of the medicament contained in the medicament container via a readable and programmable tag, wherein the tag is provided on the medicament container, and wherein the parameters are obtained via a portable app run on the mobile terminal. The method further includes displaying, on the mobile terminal, the parameters obtained via the tag. The method further includes configuring, via the portable app, at least one of the parameters of the medicament.

12 Claims, 14 Drawing Sheets

10

(56)           References Cited

U.S. PATENT DOCUMENTS

| | | | |
|---|---|---|---|
| 2015/0144702 A1* | 5/2015 | Mei | G06K 19/0775 |
| | | | 235/488 |
| 2015/0310185 A1* | 10/2015 | Shah | G16H 20/13 |
| | | | 340/10.6 |
| 2018/0039756 A1* | 2/2018 | Phipps | G16H 40/63 |
| 2018/0046833 A1* | 2/2018 | Havas | G06K 7/10386 |
| 2020/0000162 A1* | 1/2020 | Spies | H04W 4/80 |
| 2020/0386600 A1* | 12/2020 | Analytis | G01F 22/02 |
| 2022/0182481 A1* | 6/2022 | Schütz | H04B 1/59 |
| 2024/0054521 A1* | 2/2024 | Moshkovich | G06Q 30/0226 |
| 2024/0145071 A1 | 5/2024 | Hess | |
| 2024/0189874 A1* | 6/2024 | Satwicz | H04W 4/80 |
| 2024/0211624 A1* | 6/2024 | Wilbert | G06F 21/6245 |
| 2024/0220177 A1* | 7/2024 | Chen | G06F 3/0484 |
| 2024/0281633 A1* | 8/2024 | Larose | H04W 4/80 |
| 2025/0285095 A1* | 9/2025 | Martis | G06Q 20/206 |
| 2025/0294364 A1* | 9/2025 | Spector | H04W 8/08 |

* cited by examiner

10

10

10

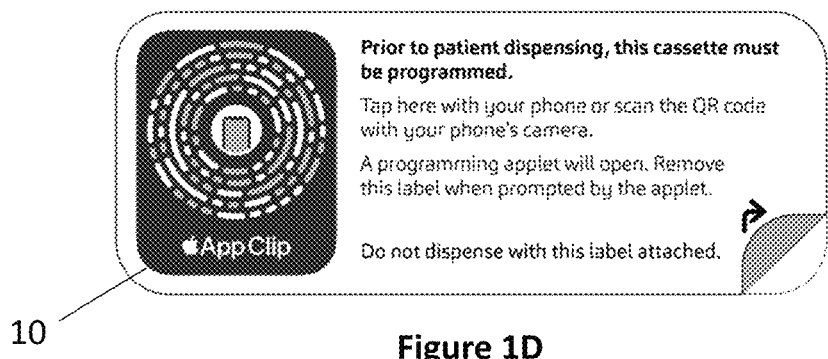
10
Figure 1D
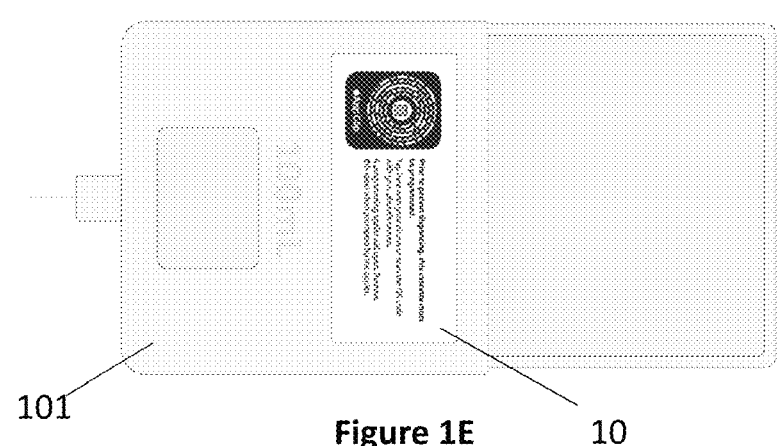
101
Figure 1E    10
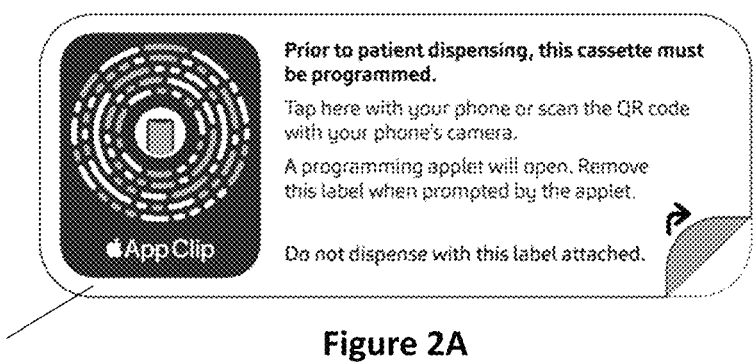
10
Figure 2A
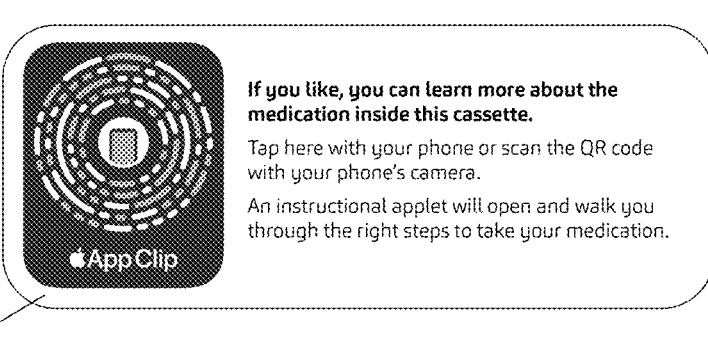
10
Figure 2B

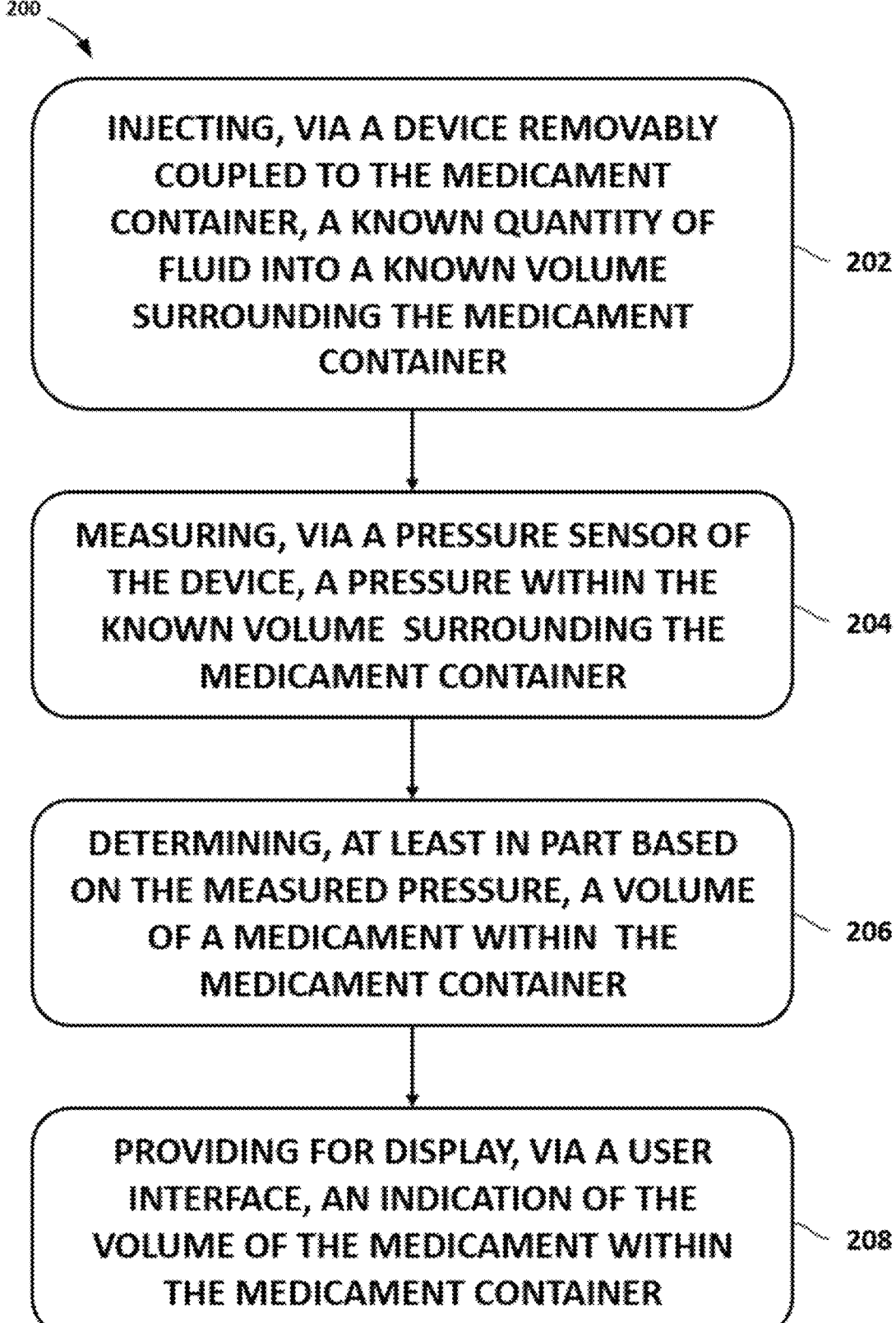

200

INJECTING, VIA A DEVICE REMOVABLY COUPLED TO THE MEDICAMENT CONTAINER, A KNOWN QUANTITY OF FLUID INTO A KNOWN VOLUME SURROUNDING THE MEDICAMENT CONTAINER — 202

MEASURING, VIA A PRESSURE SENSOR OF THE DEVICE, A PRESSURE WITHIN THE KNOWN VOLUME SURROUNDING THE MEDICAMENT CONTAINER — 204

DETERMINING, AT LEAST IN PART BASED ON THE MEASURED PRESSURE, A VOLUME OF A MEDICAMENT WITHIN THE MEDICAMENT CONTAINER — 206

PROVIDING FOR DISPLAY, VIA A USER INTERFACE, AN INDICATION OF THE VOLUME OF THE MEDICAMENT WITHIN THE MEDICAMENT CONTAINER — 208

Figure 7

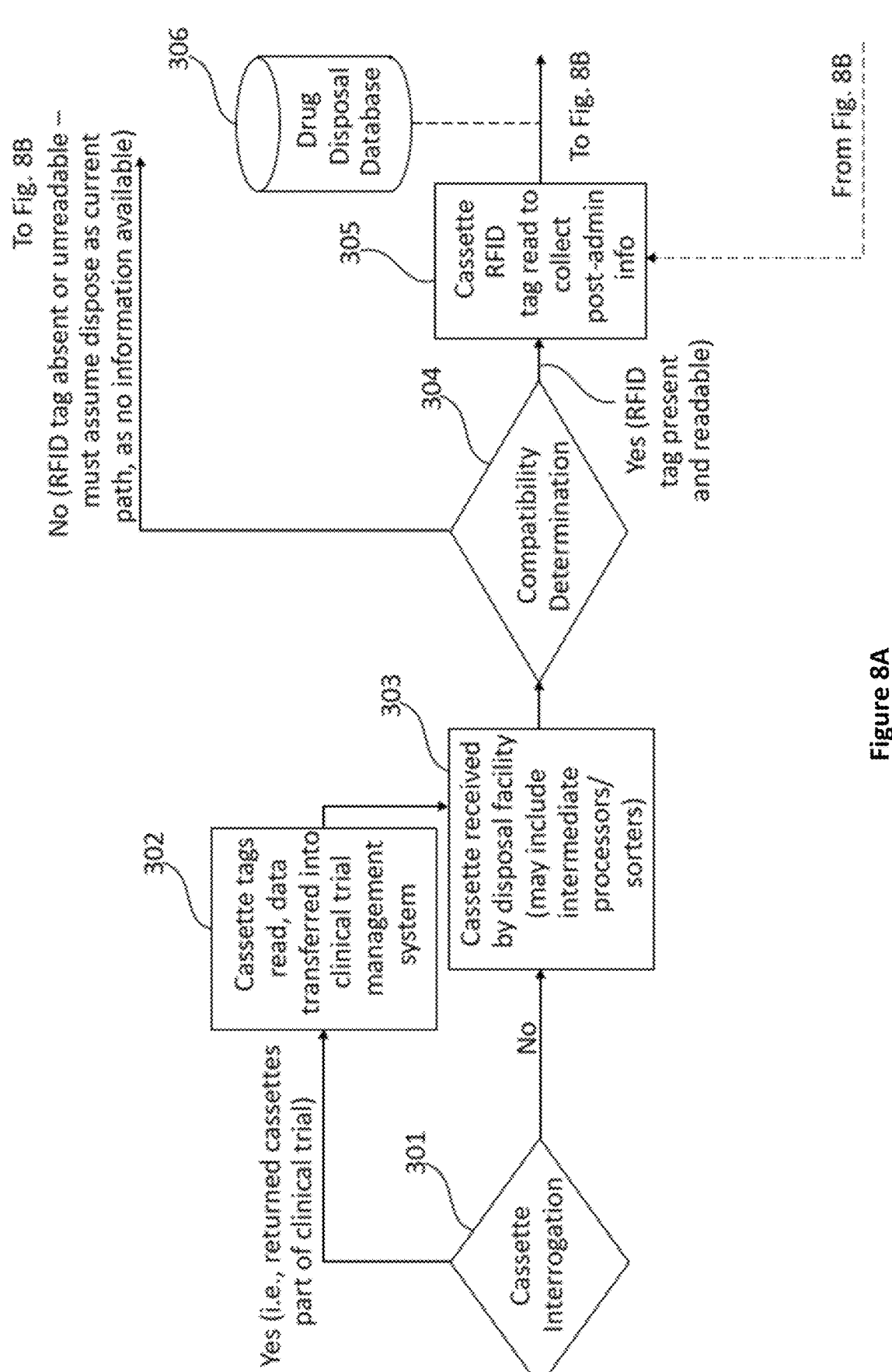

Figure 8A

306 Drug Disposal Database

To Fig. 8B

No (RFID tag absent or unreadable — must assume dispose as current path, as no information available)

305 Cassette RFID tag read to collect post-admin info

To Fig. 8B

From Fig. 8B

Yes (RFID tag present and readable)

304 Compatibility Determination

303 Cassette received by disposal facility (may include intermediate processors/sorters)

302 Cassette tags read, data transferred into clinical trial management system

Yes (i.e., returned cassettes part of clinical trial)

No

301 Cassette Interrogation

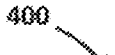
400

AFTER INJECTION OF A MEDICAMENT VIA A DEVICE, DETERMINING A VOLUME OF THE MEDICAMENT WITHIN A MEDICAMENT CONTAINER OF THE DEVICE

402

PROGRAMMING, VIA A COMMUNICATION INTERFACE ASSOCIATED WITH THE MEDICAMENT CONTAINER, AN INDICATION OF ONE OR MORE DISPOSAL PARAMETERS OF THE DEVICE BASED AT LEAST IN PART ON THE DETERMINED VOLUME OF THE MEDICAMENT WITHIN THE MEDICAMENT CONTAINER OF THE DEVICE

MEDICATION CONTAINER WITH APPLET-BASED DRUG DELIVERY PARAMETER CONFIGURATION

CROSS-REFERENCE TO RELATED APPLICATIONS

The present application claims priority to U.S. Provisional Patent Application No. 63/707,772 filed Oct. 16, 2024, the contents of which are hereby incorporated by reference in their entirety.

FIELD OF THE DISCLOSURE

The present disclosure relates to a method for configuring a drug/medicament container as well as a corresponding medicament container and system. In particular, the present disclosure relates to a medication container with applet-based drug delivery parameter configuration.

BACKGROUND

Medications may be compounded, e.g., prepared in an aseptic manner, by a pharmacy from vials or other bulk storage containers, such as vials. These medications may be manipulated to accommodate fixed dosing, weight-based dosing, or body surface area dosing using syringes, needles, and vial spikes.

Currently, a pharmacist or pharmacy technician prepares a given medicament compound (e.g., 50 ml of an oncology medication) and places it in a final container, such as a syringe, intravenous (IV) bag, or medication cassette. As each syringe of medication is added to the final container, the syringe is expelled and "pulled back" empty for later verification of the added volume. A second pharmacist then verifies the dosage, often by inspecting the syringes used. While gravimetric verification may be used, this is impractical given workflow and workload in busy compounding centers, in addition to the variable density of different medications.

Better solutions are needed to check for volumetric accuracy of filled medication containers and inspection for defects in the final medication container as part of current inspection workflows, while preserving the efficiency of staff involved in compounding operations. Additionally, as medications are shipped through a supply chain after dispensing, improved solutions are needed to examine medication containers for damage and suitability for use.

Additionally, medications such as oncology regimens may be dispensed in sequences that should be administered in order as predefined by a physician. During dispensing of a medication regimen, it is ideal for the pharmacist to encode the sequence (or verify the sequence) during dispensing. It is also ideal for the pharmacist to encode the total number of medications within a sequence. Improved solutions in this area would enable the drug delivery device to enforce the proper administration sequence by an end user, preventing mis-ordered administration or incomplete administration of all medications.

One option to provide a drug delivery device with this information is a standalone programming device, such as the one described below, the so-called "Volume Probe" device. The Volume Probe is well-suited for instances where a standalone device may be easily provided to a pharmacist, where dedicate programming equipment may be easily stored, and be close at hand when needed. This is true, for instance, when a pharmacy prepares large numbers of medication cassettes and then programs them.

However, there are instances where a standalone device is infeasible (e.g., when a smaller volume of cassettes are filled and programmed by a facility), but the same programming steps are still required. In these instances, the volume verification performed by the Volume Probe is performed by a pharmacist or pharmacy tech in the same way as the current IV practices, while providing a quantitative assessment of filled volume substituting for a visual "pull back" verification.

The present disclosure addresses the above issues and provides a flexible and easy process for checking and/or configuring medicament containers.

The present disclosure offers a complementary alternative to the Volume Probe device that preserves the programming capability while avoiding reliance on a durable volume probe device. The present approach may be especially suitable when volume probe features are not required, but the programming step alone is desirable.

SUMMARY OF THE DISCLOSURE

The present invention relates to a method for configuring a medicament container. The method comprises filling a medicament container with a predetermined amount of a medicament, or obtaining a pre-filled medicament container; obtaining, by a mobile terminal, a plurality of parameters of the medicament contained in the medicament container via a readable and programmable tag, wherein the tag is provided on the medicament container, and wherein the parameters are obtained via a portable app run on the mobile terminal; displaying, on the mobile terminal, the parameters obtained via the tag; and configuring, via the portable app, at least one of the parameters of the medicament.

Various embodiments may preferably implement the following features.

Preferably, the portable app is downloaded to the mobile terminal according to the parameters obtained via the tag.

Preferably, the tag comprises a quick response (QR) code, a near field communication (NFC) tag or a radio frequency identification (RFID) tag.

Preferably, the NFC tag or RFID tag is pre-programmed.

Preferably, the parameters comprise at least one of a medicament/drug name, an (initial) medicament volume, a residual medicament volume, a prescription dose, a time of manufacture (of the medicament), a time of filling, a dispensing sequence, medication information, pharmacy information, physician information, portable app information, or user instructions.

Preferably, the mobile terminal is handheld mobile terminal, preferably a smartphone.

Preferably, the portable app is an Instant App or App Clip.

Preferably, the tag is at least partially removable.

Preferably, the tag is a multi-layer tag, wherein at least one layer is removable and wherein each layer comprises different information.

The present invention further relates to a medicament container comprising a readable and programmable tag. The medicament container is configured for use with the method as described above.

Moreover, the present invention relates to a configurable drug dispensing system comprising a medicament container comprising a readable and programmable tag; and mobile terminal configured to perform the method as outlined above.

BRIEF DESCRIPTION OF THE DRAWINGS

Embodiments of the disclosure are now be described, by way of example only, with reference to the accompanying drawings, in which:

FIGS. 1A to 1E are schematic illustrations of labels incorporating a chip for implementing example embodiments of the disclosure.

FIGS. 2A and 2B are schematic illustrations of alternative labels incorporating a chip for implementing example embodiments of the disclosure.

FIG. 7 is a block diagram of a method, according to an example embodiment.

FIGS. 8A-8C show a schematic drawing of a process to evaluate disposal of a device after use, according to an example embodiment.

FIG. 9 is a block diagram of a method, according to an example embodiment.

DETAILED DESCRIPTION

Figure 1A:
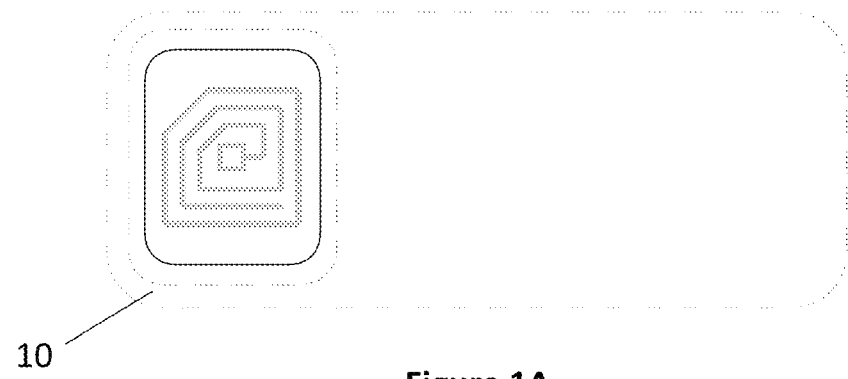

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the figures should not be viewed as limiting. It should be understood that other embodiments may include more or less of each element shown in a given figure. Further, some of the illustrated elements may be combined or omitted. Yet further, an example embodiment may include elements that are not illustrated in the figures.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, apparatus, element and method "configured to" perform a specified function is indeed capable of performing the specified function without any alteration, rather than merely having potential to perform the specified function after further modification. In other words, the apparatus, element, and method "configured to" perform a specified function is specifically selected, created, implemented, utilised, programmed, and/or designed for the purpose of performing the specified function. As used herein, "configured to" refers to existing characteristics of an apparatus, element, and method which enable the apparatus, element, and method to perform the specified function without further modification. For purposes of this disclosure, an apparatus, element, and method described as being "configured to" perform a particular function can additionally or alternatively be described as being "adapted to" and/or as being "operative to" perform that function.

As used herein, the term "drug container", "medicament container", "medication container", etc. may refer to any container configured to receive and store a drug/medicament. Thus, it may refer to any kind of medication container, such as a drug cassette, a drug cassette used with a flexible bag, a flexible bag, a glass cartridge or a syringe.

Moreover, the terms "tag" and "chip" may be used interchangeably. The tag may be readable and/or programmable (i.e., have a read/write configuration).

Also, an "applet" may generally refer to a portable app in this disclosure.

The present invention relates to a method for configuring a medicament container 101 (drug container). The method comprises filling a medicament container 101 with a predetermined amount of a medicament, or obtaining a pre-filled medicament container 101; obtaining, by a mobile terminal, a plurality of parameters of the medicament contained in the medicament container 101 via a readable and programmable tag 10 (chip), wherein the tag 10 is provided on the medicament container 101, and wherein the parameters are obtained via a portable app run on the mobile terminal; displaying, on the mobile terminal, the parameters obtained via the tag 10; and configuring, via the portable app, at least one of the parameters of the medicament.

In an embodiment, configuring may comprise, e.g., at least one of setting, changing, or reading the parameter.

In an embodiment, the portable app is downloaded to the mobile terminal according to the parameters obtained via the tag 10. The parameters/information may also be provided on the tag 10.

The tag 10 may be a QR code, an NFC tag or an RFID tag. The NFC tag or RFID tag may be pre-programmed.

In an embodiment, the parameters comprise at least one of a medicament name, an initial medicament volume, a residual medicament volume, a prescription dose, a time of manufacture (of the medicament), a time of filling, a dispensing sequence, medication information, pharmacy information, physician information, portable app information, or user instructions. That is, the parameters may relate to medicament specific information. However, other information may also be made available via the parameters, in addition or as an alternative.

Further reference is made to table 1 below. The parameters may also comprise information on whether the content of the medicament container 101 is hazardous or non-hazardous, information on participation in a clinical trial, etc. as will for example be further described with reference to FIGS. 8A-8C.

The mobile terminal may be a smartphone, personal digital assistant (PDA), a tablet or any other suitable handheld device.

The term portable app refers to an app that does not require installation. That is, the app is merely downloaded onto the mobile terminal and executed without any additional configuration required on the mobile terminal The portable app may be, for example, an Instant App (on Android devices) or App Clip (on Apple devices).

The tag 10 may be at least partially removable. The tag 10 may be formed as or included in a label. For example, the tag 10 may be a multi-layer tag 10, wherein at least one layer is removable (peel-off label). Each layer may comprise different information. For example, the layers may comprise information relevant to a pharmacy on the first layer and information relevant to a patient on a second layer.

Further, by removing a layer from the tag 10, the QR code, NFC chip or RFID chip may be removed or altered such that the information provided thereon may not be changed and/or read.

For example, each layer may comprise a different QR code leading to different information. Also, an RFID blocking layer, e.g., a metallic sheet, may be provided to prevent readout of another chip located below the blocking layer. This will be further described in the context of FIGS. 10A and 10B.

An embodiment also encompasses a medicament container 101 (apparatus/device) for use with the method described above. The medicament container 101 comprises a readable and programmable tag 10. As outlined above, the medicament container 101 may be filled or may be delivered in a pre-filled state.

Further, the present invention encompasses a configurable drug dispensing system comprising a medicament container 101 comprising a readable and programmable tag 10; and a mobile terminal configured to perform the method described above.

The invention may provide some or all of the below features and advantages.

Provides sequence programming capability for medication cassettes/reservoirs similar to Volume Probe without use of a durable, dedicated programmer.

Uses existing technology in modern smartphones (portable apps such as instant apps, app clips), without need for a device-specific mobile terminal or computer system integration.

Allows pharmacy programming at point of dispensing within existing workflow.

Provides a QR code or embedded RFID/NFC chip in a package that drives a programming step during dispensing by a pharmacist.

Does not presume or require an electronic health record integration, as it is completely standalone, eliminating need/burden of integration with healthcare IT systems.

Provides a double-layer label that removes and/or reduces re-programming possibility from patient after removal by pharmacist.

Provides a portable app such as an instant app or app clip that is continuously updated (add features, correct bugs, accommodate new reservoir designs) as part of natural operation at each use, so always includes newest functionality, without managing external programmers, upgrades, revalidation.

Allows functionality to be gradually added to drug delivery system by providing more capability over time to write/overwrite more content as new features are added.

Optionally provides instructional content to an end user of the device after programming and dispensing by a pharmacist or HCP; this may be internet-delivered, while the core device control is completely offline without an internet connection required.

Optionally incorporates "freeze" functionality to allow reprogramming until point of dispensing, but disallows patient reprogramming.

Allows only authorised users (via login, token, RFID private key) to access RFID read/write for programming. That process owned/licensed by a provider, with the baked in functionality to again push up a record of RFID access any time it is used; no end users can read or write the RFID data without the provider having a record.

A drug delivery device is generally provided with a medication container, such as a drug cassette used with a flexible bag, a glass cartridge or a syringe. Other reservoirs are of course possible as well. The present disclosure is, however, not limited to (automated/semi-automated) drug delivery devices but may also be employed for filling of medication bags or pre-filled medication bags.

The medication container may be provided with at least one tag 10 (e.g., an RFID/NFC chip or "chip" 10) that is readable, programmable, and/or reprogrammable at one or more stages of use. The chip may be designed to cooperate with (i.e., activate) an applet (portable app, Instant App, App Clip), as described below. There may also be multiple chips, for instance a first chip to activate an applet (described below) and a second to contain information related to the drug delivery device. There may also be multiple chips, one or more of each corresponding to a different applet (e.g., an iOS applet and an Android applet); alternatively, a single chip may be configured to allow launch of the appropriate applet platform based on the smartphone scanning the chip.

The chip may be attached to the primary container itself, in a surrounding element (e.g., outer housing or interior cavity), or in another desirable (i.e., predictable, predetermined) position for reading later on in the process.

The chip may be programmed using a portable app (an app clip, instant app), a small piece of software loaded to a smartphone on demand during use of the apparatus. As noted above, such portable app does not require installation. Programming elements correspond to one or more aspects of drug delivery, either for a single cassette, or a cassette in sequence with other similarly designed cassettes (e.g., medication regimen).

Pharmacy Filling, Verification, and Dispensing

The method/medicament container 101 (apparatus) may be designed to fit existing pharmacy workflows, particularly those a) used for sterile compounding (filling of empty reservoirs with medication), b) used for dispensing of ready to use (i.e., manufacturer prefilled) specialty medications, such as biologics, and c) used for filling of investigative medications used for clinical trials.

To use the medicament container 101 (cassette, bag, etc.), an end user (e.g., a pharmacist, personnel at a manufacturing plant, patient, etc.) performs some or all of the following steps (steps may be omitted, skipped, or reordered based on pharmacy preparation practices/workflows, or regional differences, such as regulations):

1. If the chip is provided on the medicament container 101, unpackage empty or prefilled physical cassette from outer packaging, exposing a chip and instructional content to a pharmacist or pharmacy technician.
2. If the medicament container 101 is to be filled, fill the cassette with medication, using standard pharmacy processes (e.g., from a vial, using a syringe and filling adapter, such as described in WO 2024/110558 A1.
3. If the medicament container 101 is to be filled, verify the medication volume if desired, using standard pharmacy filling practices (e.g., visual inspection) or a physical volume probe without programming capability (e.g., that described in the appendix).
4. Prompted by instructional content, pharmacist or pharmacy technician scans chip with phone (e.g., by NFC) or QR code (located on physical cassette or outer box) with smartphone camera.
5. Most current app clip is downloaded onto the smartphone, including most recent version of all functionality for programming applet. Optionally, a login procedure may be implemented to prevent unauthorised scanning and inadvertent or undesired reprogramming.
6. Optionally, applet reads the chip and displays on the smartphone screen any default or pre-programmed values that are provisioned on the chip (i.e., at time of manufacture, from a previous programming instance, or both).
7. The end user configures (i.e., sets or selects) one or more parameters in applet on smartphone screen, including new values, reset of preexisting values to default values, overwrite of existing values (e.g., defaults), or combinations thereof
8. The end user (either the first end user of Step 7, or another end user, such as an independent verifier) confirms the values are the desired ones
9. Optionally, either of the users of Steps 7 and/or 8 may indicate the to-be-programmed values are "finalised" and the cassette should be write-locked after programming
10. Either of the users of Steps 7 and/or 8 activates the programming sequence on the applet, allowing the smartphone and applet to reprogram the chip with the values set in Step 7 and confirmed in Step 8
11. The applet optionally reads back the values set in Step 9 and confirms they were set in accordance with Step 7
12. If the comparison performed of Step 11 is successful, the applet displays a message on the smartphone screen that the medication cassette is ready for dispensing
13. If the comparison performed of Step 11 is unsuccessful, the applet displays a message on the smartphone screen that the medication was improperly reprogrammed, offering the opportunity to re-program the cassette (e.g., repeat Step 10 onwards) or notify the end user that the cassette should not be dispensed, but discarded 14. Optionally, if the values were configured as finalised in Step 9, the applet displays a message on the smartphone screen to remove the pharmacy label and programming instructions.
15. If Step 14 is performed, the NFC chip itself (having been programmed) is retained on the cassette, but is not apparent to the end-user (to avoid subsequent scanning and inadvertent or undesired reprogramming). Optionally, Step 14 may also remove the security key or applet token that allows access to the RFID write interface.
16. Optionally, if Step 14 is performed, then subsequently and optionally expose a second layer of an instructional sticker to be visible to a patient (launches instructional app clip with med info, instructions, etc.). Notably, this is reference information for a patient, while still allowing the RFID to locally store encoded parameters that communicate with the drive system reader with the device offline (no internet connection is needed for administration).
17. If the chip is a separate component from the physical cassette, and is programmed in a separate location from the cassette (e.g., outside the pharmacy cleanroom), it may be applied to the cassette.

As noted above, the steps are not to be construed as limiting to the present invention or implying a certain order of the steps but are merely used for exemplary and explanatory purposes.

Programming Instructions & Chip

The chip is interrogated by the drug delivery device (e.g., by antenna or passive excitation) and carries parameters associated with one or more aspects of the drug delivery for that medication container, e.g., as described in WO 2024/052528 A1.

Each chip may contain different parameters (or different parameter values) for different medication containers, which is particularly advantageous when multiple medications are used, as in a medication sequence or regimen. Exemplary parameters are listed above and in table 1 below.

The chip may be a separate sticker (as shown in FIG. 1A), which may also contain human-readable affordances, such as the ordinal sequence number, which may be used if the chip is attached directly to the medication container.

Figure 1B:
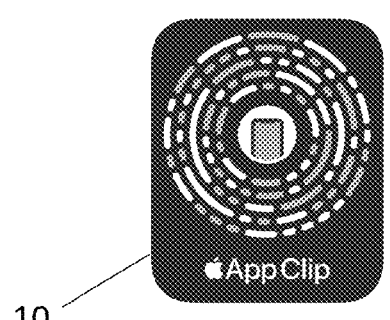

The inner rounded outline of FIG. 1A may be covered by a generic applet code (e.g., for iOS as shown in FIG. 1B). Further, additional context on who should scan it, when they should scan it, or why they should scan it may be provided on the tag 10/label.

Figure 1C:
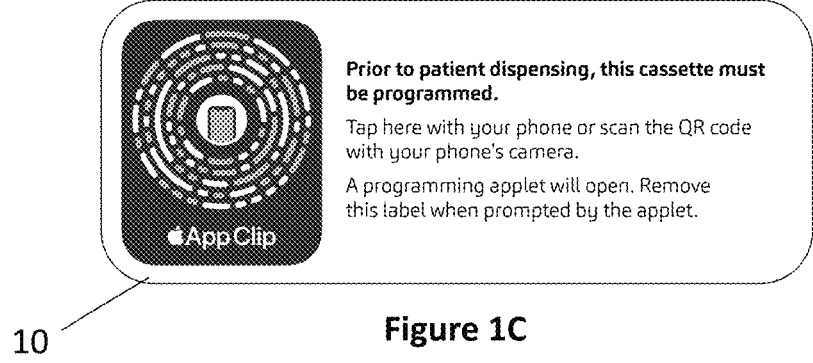

To improve intuitiveness, as shown in FIGS. 1C & 1D, the tag 10 may also be adapted to provide instructional content, driving an end user pharmacist or pharmacy technician to scan the code with their phone, which then launches an app clip. The chip may also be integrated into such a structure during manufacturing.

The exemplary text on the tag 10 shown in FIG. 1C reads: "Prior to patient dispensing, this cassette must be programmed. Tap here with your phone or scan the QR code with your phone's camera. A programming applet will open. Remove this label when prompted by the applet."

The tag 10 of FIG. 1D additionally notes: "Do not dispense with this label attached."

The chip may be placed under a permanent label as seen in FIG. 1B (with the label outline shown in gray dashed line of FIG. 1A), under a wholly removable label as shown in FIG. 1D, as part of a partially removable label, or embedded into a medication container 101 as shown in FIG. 1E (using the label of FIG. 1C). Although in FIG. 1E, a flexible medicament bag 101 is shown as the medicament container 101, the present disclosure is not limited to this configuration and equally encompasses other types of medicament containers such as cassettes, as described throughout the specification.

In these embodiments, the label element (tag 10) may also serve to communicate the location of the chip to a pharmacist of pharmacy technician. Selective removal of the label may retain the chip but conceal the purpose from an end user of the device, such as a patient.

Previous discussion has been confined on use of the apparatus in pharmacy setting during dispensing. However, this need not be the only use case. The present invention may be adapted to allow programming by a pharmacist and subsequent interrogation by a patient using their own smartphone and applet.

As shown in FIGS. 2A and 2B, a two-layer tag 10 may also be provided as an alternative to FIGS. 1A-1E. A first layer, shown in FIG. 2A and corresponding to the tag 10 of FIG. 1D, may provide information to a pharmacist dispensing, similarly to FIGS. 1A-1E. However, the first layer may be removed after programming, revealing the second layer, depicted in FIG. 2B.

This second layer shown in 2B reads: "If you like, you can learn more about the medication inside this cassette. Tap here with your phone or scan the QR code with your phone's camera. An instructional applet will open and walk you through the right steps to take your medication."

When scanned by a patient's smartphone, the second layer may present alternative, patient-focused information about the medication within the container (or medication parameters programmed by pharmacy or a pharmaceutical manufacturer) after dispensing and programming as described above. The instructional content could be an applet link to instructional content, training material, display of the medication parameters, link to download and install the full app, or other relevant information.

Chip Data Structure

At least one chip provided has a predefined data structure related to one or more aspects of medication delivery. For instance, this could include the number of medications in a sequence, the ordinal cassette number, etc. This could also include information related to a prefilled medication or clinical trial medication. Many such values are possible, with additional illustrative and non-limiting examples shown in table 1 below.

As seen in table 1, values may optionally be pre-populated as default (e.g., default flow rate for the medication container); others may be unpopulated and programmable (sequence number, total number of containers in the sequence). The values may also optionally vary based on the setting in which a cassette is used, such as in a clinical trial, in an empty (pharmacy filled), or prefilled presentation. Different cassettes may also have different parameters pre-populated, and some cassettes may not have any parameters pre-populated.

Also, although not shown here, portions of the data structure may be provisioned or populated but need not be used. For instance, this may include provision for later storage (i.e., programming or reprogramming) of a cassette's disposal status information, as detailed in the appendix.

Cooperating Programming Applet

In one or more embodiments, the tag 10 or chip described previously is configured to cooperate with a smartphone applet, a term used herein for simplicity, but colloquially known as an "App Clip" (iOS) or "Instant App" (Android).

Such applets provide a subset of a full application functionality quickly accessible format, allowing users to complete predefined, simple tasks rapidly without downloading the full app. In other words, applets are designed to focus on a specific task that needs to be completed "on demand". In consumer applications, for example, this could include paying for parking, ordering a coffee, or parcel tracking. As these examples illustrate, applets are generally small payloads (e.g., 10 MB) and thus download and launch quickly (in seconds), avoiding the need to find the correct application, install an application, or download an application.

Put another way, applets are a useful tool to remove friction for commonly (or infrequently) performed predefined tasks. Advantageously, use of applets does not require download of a full app, which allows it to be opened and used quickly. Moreover, applets are cached once downloaded for a short period of time, then discarded from smart phone memory; at each instance, the applet is re-downloaded.

Herein, applet is used in a generic sense describe smart phone software configured to cooperate with one or more physical medication cassettes to program one or more aspects of medication delivery in a straightforward, intuitive manner. The advantageous features of applets are used in the present invention to:

Allow programming of frequently-used parameters onto a cassette without the need to download software, create an account, have dedicated capital equipment Avoid programming cassettes without having the most current software always at hand Selectively expose parameters based on the context of use and type of cassette (e.g., pharmacy filled cassette vs. prefilled cassette)

Optionally, upload information (likely in de-identified format) to the digital cloud, for diagnostic, statistical trending, or post-market surveillance purposes In an embodiment, the tag 10 or chip may comprise some or all of the information/parameters listed in the table 1 below.

TABLE 1

|  | Clinical Trial Application | Pharmacy Filled Application | Manufacturer Filled Application |
|---|---|---|---|
| Default Values (Static) (Unchangeable by applet) | Medication container max volume Clinical trial study condition (randomisation) | Medication container max volume Flow rate (mL/min) | Medication container max volume Medication name, dose, concentration Flow rate (mL/min) Needle pullout detection enabled |

TABLE 1-continued

|  | Clinical Trial Application | Pharmacy Filled Application | Manufacturer Filled Application |
|---|---|---|---|
|  |  |  | Occlusion detection enabled<br>Device mimic profile |
| Default Values (Dynamic) (Reprogrammable by applet) | Study sponsor | Medication name, dose, concentration | n/a |
| Programmable Values (Configurable by applet) | Placebo or study medication<br>Study identifier<br>Medication position within ordinal sequence in regimen<br>Number of total medications within regimen<br>Flow rate (mL/min)<br>Medication name, dose, concentration | Medication position within ordinal sequence in regimen<br>Number of total medications within regimen<br>Beyond use date (BUD) | Medication position within ordinal sequence in regimen<br>Number of total medications within regimen |
| Inaccessible Values (Present on RFID tag, but not exposed in particular use case by applet) |  | Needle pullout detection enabled<br>Occlusion detection enabled<br>Device mimic profile |  |

The present disclosure further relates to apparatus, systems, and methods for drug delivery devices, and more particularly to improved apparatus, systems, and methods to verify a volume of a medicament within a medicament container for use with a drug delivery device.

Medications may be compounded—prepared in an aseptic manner—by pharmacy from vials or other bulk storage containers, such as vials. These medications are manipulated to accommodate fixed dosing, weight-based dosing, or body surface area dosing using syringes, needles, various adapters, and vial spikes.

Currently, a pharmacist or pharmacy technician prepares a given medicament compound (e.g., 50 ml of an oncology medication) and places it in a medicament container, such as a syringe, IV bag, or medication cassette. As each syringe of medication is added to the final container, the syringe is expelled and "pulled back" empty for later verification of the added volume. A second pharmacist then verifies the dosage, often by inspecting the syringes used. While gravimetric verification may be used, this is impractical given workflow and workload in busy compounding centers, in addition to the variable density of different medications.

Better solutions are needed to check for volumetric accuracy of filled medication containers and inspection for defects in the final medication container as part of current inspection workflows, while preserving the efficiency of staff involved in compounding operations. Additionally, as medications or medication containers are shipped through a supply chain before, during, or after dispensing, improved solutions are needed to examine medication containers for damage and suitability for use.

Additionally, medications such as oncology regimens may be dispensed in sequences that should be administered in order as predefined by a physician. During dispensing of a medication regimen, it is ideal for the pharmacist to encode the sequence (or verify the sequence) during dispensing to ensure proper/safe dispensing to a patient. It is also ideal for the pharmacist to encode the total number of medications within a sequence, also for quality control and safety purposes. Improved solutions in this area would enable the drug delivery device to enforce the proper administration sequence by an end user, preventing mis-ordered administration or incomplete administration of one or more medications.

An embodiment of the present invention is directed to improved apparatus, systems, and methods to verify a volume of a medicament within a medicament container for use with a drug delivery device. More particularly, the present disclosure is directed towards a standalone device for empirical verification of a filled volume prior to dispensing a compounded/filled medicament container to a patient and/or after dispensing the compounded/filled medicament container to the patient.

As such, the present disclosure provides a device configured to be removably coupled to a medicament container. The device includes including a pump, a battery configured to supply power to the pump, at least one pressure sensor, at least one memory storage element, at least one processor, and data storage including program instructions stored thereon that when executed by the at least one processor, cause the drug delivery device to perform functions. The functions include (i) injecting, via the pump, a known quantity of fluid into a known volume surrounding the medicament container, (ii) measuring, via the pressure sensor, a pressure within the known volume surrounding the medicament container, (iii) determining, at least in part based on the measured pressure, a volume of a medicament within the medicament container, and (iv) providing for display, via a user interface, an indication of the volume of the medicament within the medicament container.

Further, the present disclosure provides a method comprising (i) injecting, via a device removably coupled to the medicament container, a known quantity of fluid into a known volume surrounding the medicament container, (ii) measuring, via at least one pressure sensor of the device, a pressure within the known volume surrounding the medicament container, (iii) determining, at least in part based on the measured pressure, a volume of a medicament within the medicament container, and (iv) providing for display, via a user interface, an indication of the volume of the medicament within the medicament container.

Further, the present disclosure provides a method comprising (i) after injection of a medicament via a device, determining a volume of the medicament within a medicament container of the device, and (ii) programming, via a communication interface associated with the medicament container, an indication of one or more disposal parameters of the device based at least in part on the determined volume of the medicament within the medicament container of the device.

As noted above, the following description may be used in conjunction with or as an alternative to the embodiments described above.

In FIGS. 7-9, referred to above, the blocks may represent operations and/or portions thereof and lines connecting the various blocks do not imply any particular order or dependency of the operations or portions thereof. It will be understood that not all dependencies among the various disclosed operations are necessarily represented. FIGS. 7-9 and the accompanying disclosure describing the operations of the method(s) set forth herein should not be interpreted as necessarily determining a sequence in which the operations are to be performed. Rather, although one illustrative order is indicated, it is to be understood that the sequence of the operations may be modified when appropriate. Accordingly, certain operations may be performed in a different order or simultaneously. Additionally, those skilled in the art will appreciate that not all operations described need be performed.

The present disclosure is directed towards a standalone device for determination of a filled volume prior to dispensing a compounded/filled medicament container to a patient and/or after dispensing the compounded/filled medicament container to the patient. The systems and methods described herein incorporate a volume verification device into pharmacy workflows to improve safety and efficiency of medicament volume verification. Such a volume verification device may be used to determine the filled volume (if any) without a priori knowledge of the filled volume or medication therein.

Figure 3:
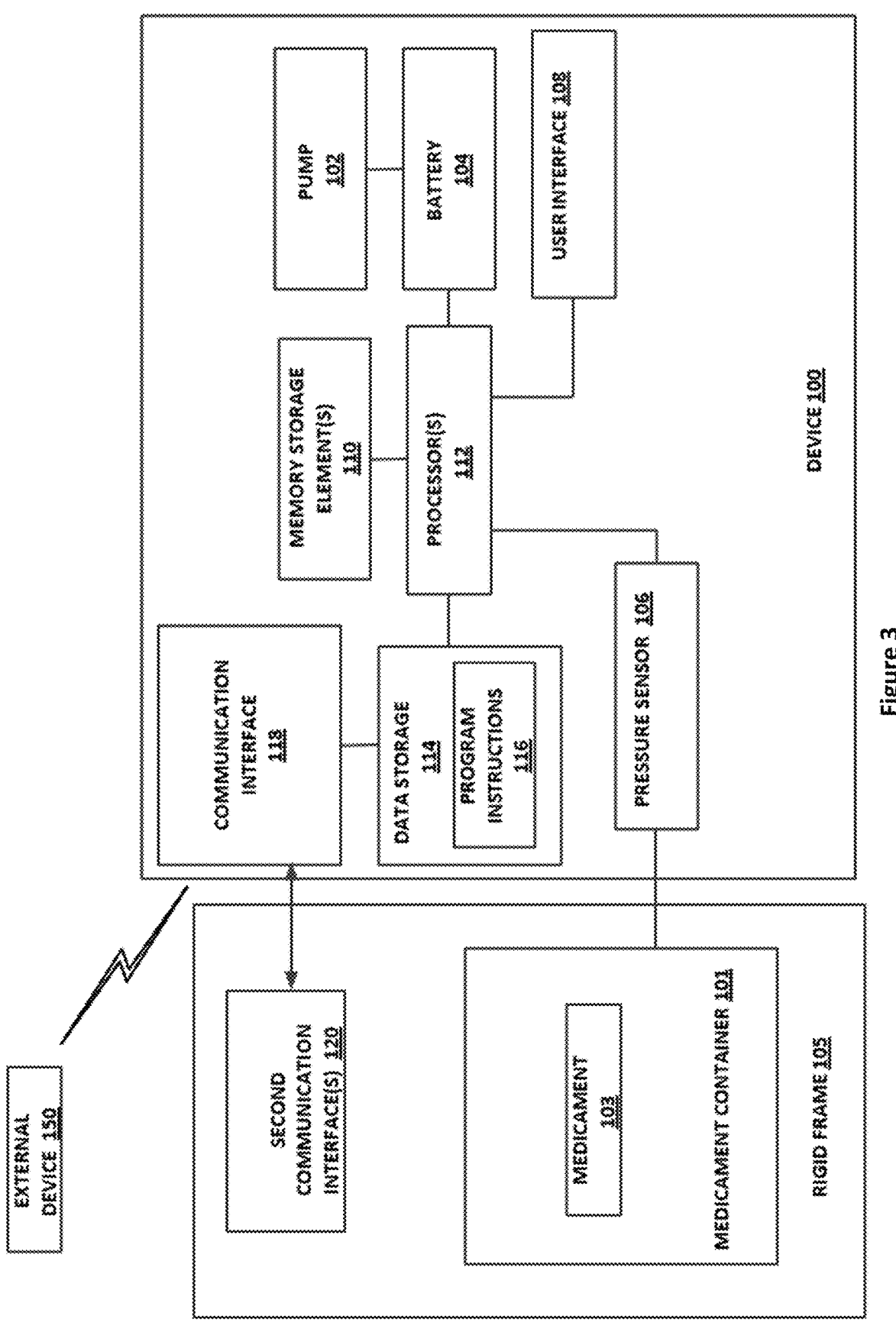
FIG. 3 illustrates a simplified block diagram of a device, according to an example embodiment.
Figure 4B:
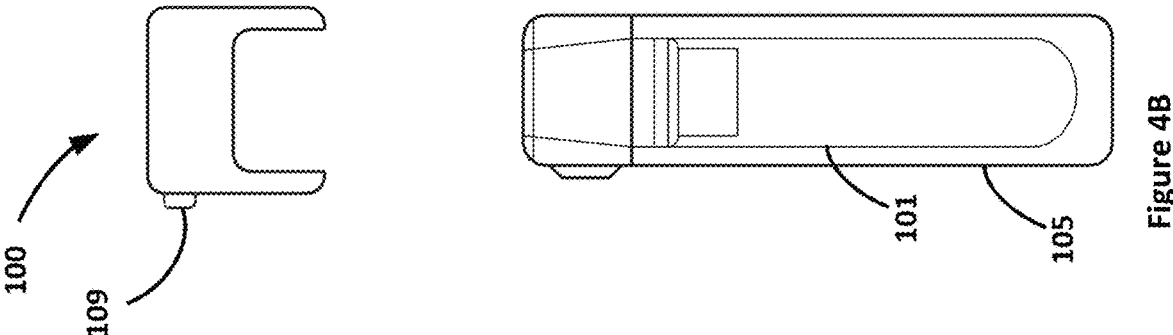
FIG. 4B illustrates a side view of the device and the medicament container of FIG. 4A, according to an example embodiment.
Figure 4A:
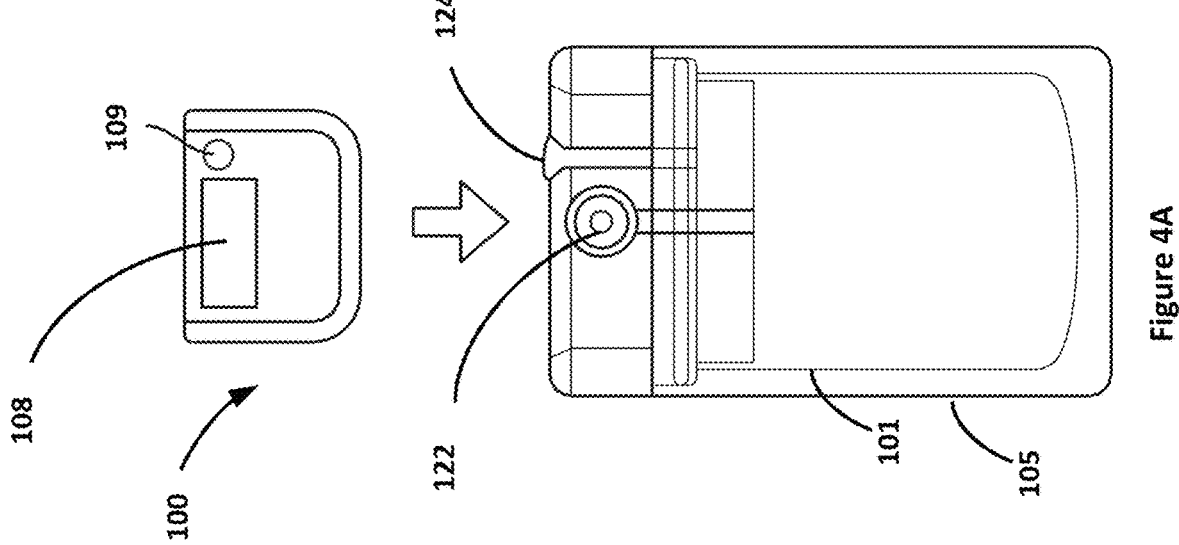
FIG. 4A illustrates a front view of an example device and an example medicament container, according to an example embodiment.
Figure 4D:
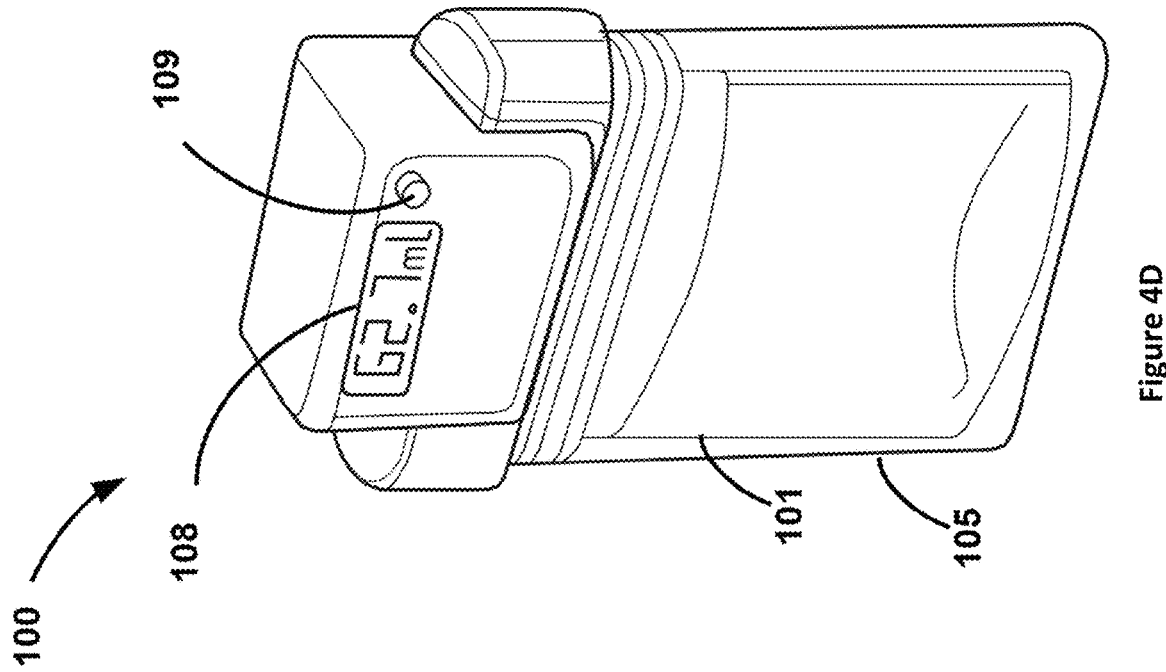
FIG. 4D illustrates a perspective view of the device and the medicament container of FIG. 4A with the device removably coupled to the medicament container, according to an example embodiment.
Figure 4C:
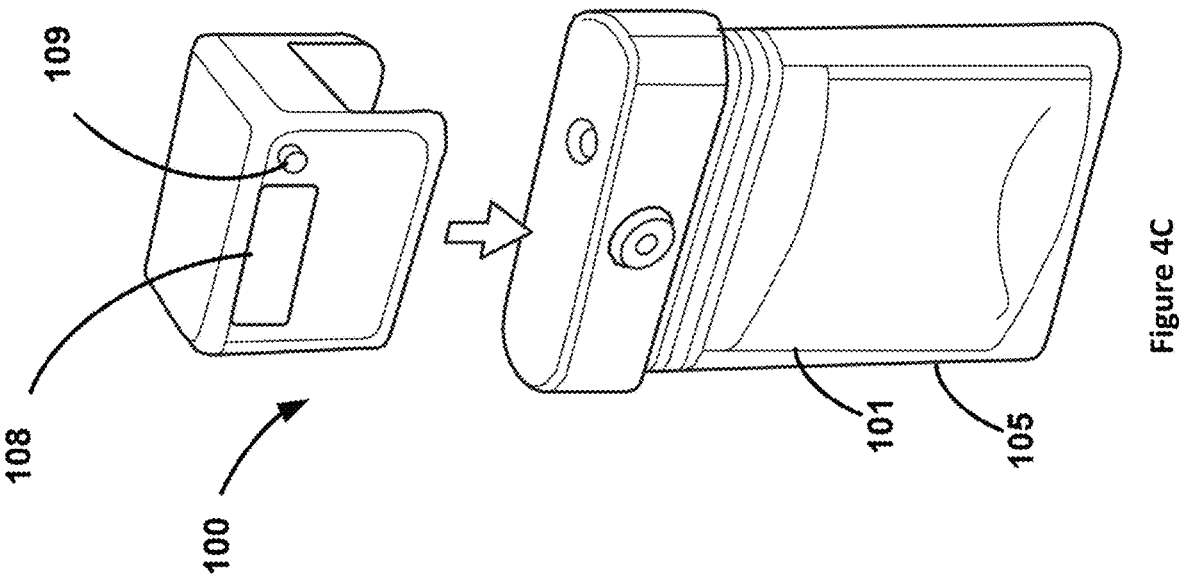
FIG. 4C illustrates a perspective view of the device and the medicament container of FIG. 4A, according to an example embodiment.

With reference to the figures, FIG. 3 illustrates a simplified block diagram of a device 100, according to an example embodiment. The device 100 is configured to be removably coupled to a medicament container 101, as discussed in additional detail below. In one example, the medicament container 101 comprises a flexible bag contained within a rigid frame 105 (e.g., a cassette). As shown in FIG. 3, the device 100 includes a pump 102 and a battery 104 configured to supply power to the pump 102. The pump 102 may comprise a piezoelectric air pump, as a non-limiting example. The device 100 further includes at least one pressure sensor 106 used to measure a pressure within a known volume surrounding the medicament container 101 (i.e., the flexible bag), as discussed in additional detail below. The (known) volume surrounding the medicament container 101 may refer to a volume between an outer surface of the flexible bag containing the medicament/drug and an inner surface of a cassette (e.g., the medicament container 101 or the rigid frame 105) provided around the bag. Thus, when it is referred to the (known) volume surrounding the medicament container 101, it may also encompass a volume/space between a medicament bag and a casing surrounding said medicament bag.

The medicament container 101 may be air tight. Based on the above volume, a residual amount of medicament may be determined. That is, the larger the volume, the smaller the amount of medicament remaining in the flexible bag.

The known volume may be predetermined based on a total (interior) volume in the medicament container 101 and a volume of the medicament (plus, if applicable, a volume of the medicament bag) stored in the container 101. In particular, the known volume may be the total volume minus the medicament volume.

The device 100 also includes a user interface 108, such as an optical see-through display, an optical see-around display, a video see-through display, or a touch-screen display, as non-limiting examples. The user interface 108 may further include a button 109 or other user input means, as shown in FIGS. 4A-6. Alternatively, the user interface 108 may be provided on a separate device, such as an electronic health record screen, companion application on a smartphone, or other computing device, as non-limiting examples.

The device 100 further includes at least one memory 110 (memory storage element). The at least one memory 110 can include any type of memory now known or later developed including but not limited to volatile memory (such as RAM), non-volatile memory (such as ROM, flash memory, etc.) or any combination thereof. The device 100 also includes at least one processor 112 and data storage 114 including program instructions 116 stored thereon that when executed by the at least one processor 112, cause the device 100 to perform functions. Although various components of the device 100 are shown as distributed components, it should be understood that any of such components may be physically integrated and/or distributed according to the desired configuration of the system.

Depending on the desired configuration, the at least one processor 112 can be any type of processor including, but not limited to, a microprocessor, a microcontroller, a digital signal processor, or any combination thereof.

In particular, the functions include (i) injecting, via the pump 102, a known quantity of fluid into a known volume surrounding the medicament container 101, (ii) measuring, via the at least one pressure sensor 106, a pressure within the known volume surrounding the medicament container 101, (iii) determining, at least in part based on the measured pressure, a volume of a medicament 103 within the medicament container 101, and (iv) providing for display (i.e., displaying), via the user interface 108, an indication of the volume of the medicament 103 within the medicament container 101. In one example, the fluid injected into the known volume is a compressible fluid such as (ambient) air or an ideal gas (e.g., hydrogen as a non-limiting example). In one example, the functions further include removing fluid from the volume surrounding the medicament container 101 to return the known volume surrounding the medicament container 101 to atmospheric pressure (i.e., establish equilibrium/balance of a pressure of the internal known volume with atmospheric pressure). This may be done, e.g., by opening a valve to establish atmospheric pressure within the cassette/medicament container 101. Also, a controlled amount of fluid may be expelled from the known volume, thereby lowering the pressure in the known volume.

As noted above, the known volume may be a volume within an air tight container/cassette containing a (flexible) medicament bag within. By injecting fluid into the known volume, a medicament stored in the medicament bag may be expelled by pressurising the outside of the bag. Further, a determination on a residual amount of medicament may be made based on the volume and/or pressure (injected volume, known volume and pressure).

In one example, the volume of the medicament 103 within the medicament container 101 may be determined using the ideal gas law and its simplifications. Application of the ideal gas law is critical to volumetric system actions, (flow rate control, medication volume sensing), as volumes of abstract geometry cannot be directly probed by known cost-effective sensing methods. For a commercial presentation of this device, it is unlikely, however, that the system uses pure ideal gases; use of ambient air is highly advantageous. So, while the ideal gas law, PV=nRT, applies directly to ideal gases, it is not a perfect representation of ambient air. Introducing a compressibility factor, z, to the Ideal Gas Law allows for general application to ambient air; PV=znRT. At the foreseeable system temperatures and pressures (280-310 K, 1-10 bar), 0.9992<z<1.0004, and therefore air can be approximated as an ideal gas.

To further simplify the equation, it is evident that the temperature term T does not have great influence, since the foreseeable values are in a tight window of 280-310K. Even in the event that the volume of air starts at 280K and rises to 310K over the course of a volume-sensing action, the temperature term alone could not cause more than a +/−5% reduction in volumetric assessment accuracy. That is a very conservative case, as the control air temperature is likely to be dominated by the medicament container 101 enclosure temperature and indirectly by ambient room temperature (as the medicament container 101 has more internal surface area than the drug reservoir to conduct to the air). Furthermore, as the rigid frame, or "cassette" which contains the bag is vented to the ambient air throughout the preceding pharmacy workflow, the air within the cassette would be approximately equivalent to room temperature, which would not introduce any temperature-based inaccuracies. Allowing +/−5% measurement sensitivity in this step is likely acceptable clinically, and notably, a much greater sensitivity than volume verification methods in current practice, which contain no capability of empirical assessment. However, introduction of a system air temperature sensor, or a local cassette air temperature sensor would remove uncertainty due to a temperature difference between room-temperature air and the cassette's internal air. Obviously, although injections and infusions are used herein, accuracy of the system may be determined on a case by case basis, given a physiologic route of administration and appropriate clinical parameters thereto.

In a preferred system control model, the reduced ideal gas law becomes PV∝nR. Since nR represents the number of molecules in the system, or mass, m, the reduction is therefore PV∝m; V∝m/P. To determine void volume of the system at any given time, the system must keep track of the transferred mass to the control volume, e.g., via a known relationship between the drive parameters and the injection mass or via a comparative, proxy control region of known volume that air is dispensed from, such as a traditional accumulator model. In a volume assessment step, it is critical that the unfilled volume of the medicament cassette and the device's internal air volume is known. This is because the volume assessment device is assessing the system's air volume, and the filled volume of medicament is equal to the difference between an unfilled system's air volume and the filled system's air volume.

The ability to determine the volume of the medicament 103 within the medicament container 101 is particularly advantageous as the system is insensitive to initial fill, and can be determined based only on the change in mass and without knowing the initial fill volume (i.e., no programming step is required). As such, the direct calculation of the volume of medicament 103 in the medicament container 101 allows the unique benefit of a blind, third-party verification of medication added to the medicament container 101, which is not a capability that exists in current pharmacy best practices for flexible drug reservoirs, e.g., bags for IV administration. In one application of this concept, the volume of medicament 103 in the medicament container 101 can be independently verified at a pharmacy with a dedicated device, without the introduction of human error, providing distinct benefit to pharmacy quality control practices.

In one example, the indication of the volume of the medicament 103 within the medicament container 101 comprises a numerical value (e.g., an indication of a number of mL). In another example, the indication of the volume of the medicament 103 within the medicament container 101 comprises providing an indication to a verifying pharmacist based on whether the filled volume is within the expected dose (± any tolerance, if desired). In other words, the pharmacist may, informed by data from the indicated volume and/or tolerance, choose to accept (i.e., dispense to a patient for later administration) or reject (i.e., do not dispense to a patient for later administration) the filled reservoir. In one example, the device 100 further includes at least one first communication interface 118 configured to receive information from at least one second communication interface 120 positioned on a rigid frame 105 of the medicament container 101 when the device 100 is removably coupled to the medicament container 101 via the rigid frame 105. In another example, the at least one second communication interface 120 is positioned directly on the medicament container 101. Such information may include an identification and/or characteristics of the medicament 103 in the medicament container 101. The at least one first communication interface 118 and the at least one second communication interface 120 may contain hardware to enable a communication link therebetween, such as processors, transmitters, receivers, antennas, etc., as discussed above. In one example, the communication link between the at least one first communication interface 118 and the at least one second communication interface 120 is a wired connection. In another example, the communication link between the at least one first communication interface 118 and the at least one second communication interface 120 is a wireless connection such as radio frequency identification (RFID), near-field communication (NFC), Bluetooth, Bluetooth low energy (BLE), Ultra wide band (UWB), wireless fidelity (Wi-Fi), cellular communication, and infrared (IR), as non-limiting examples. In one example, the program instructions 116 further cause the device 100 to transmit, via the first communication interface 118, the volume of the medicament 103 within the medicament container 101 to an external device 150. As outlined above, the volume of the medicament 103 may be determined based on the known volume and the measured pressure within the known volume. The transmitted volume of the medicament 103 may refer to a (residual) amount of medicament 103 present in the medicament container 101.

The external device 150 may be any type of device that can receive data and display information corresponding to or associated with the data. For example, the external device 150 may be a mobile phone, a tablet, or a personal computer as examples. As such, the volume of the medicament 103 within the medicament container 101 may be transmitted to the prescribing facility, the dispensing facility, the drug manufacturer, the device manufacturer, and/or clinical trial administrator(s), as non-limiting examples.

In one example, the program instructions 116 further cause the device 100 to (i) receive an indication of an expected volume of the medicament 103 within the medicament container 101, and (ii) compare the determined volume of the medicament 103 within the medicament container 101 with the expected volume of the medicament 103 within the medicament container 101. In one example, the indication of the expected volume of the medicament 103 within the medicament container 101 is received via a user input at the user interface 108. In another example, the indication of the expected volume of the medicament 103 within the medicament container 101 is received via the second communication interface 120 on the rigid frame 105 at least partially surrounding the medicament container 101. In one specific example, the second communication interface 120 on the rigid frame 105 at least partially surrounding the medicament container 101 comprises a RFID/NFC chip (as described above, also referred to as a RFID/NFC tag, not shown). As such, the device 100 may read an embedded RFID/NFC chip on the rigid frame 105 and/or the medicament container 101 to set the expected dose within the device 100 to verify against the filled volume within the medicament container 101. After measurement, the device 100 may be configured to program the embedded RFID/NFC chip on the rigid frame 105 with the measured volume of the medicament 103 in the medicament container 101. Other encoding methods than RFID/NFC may be used, as will be apparent to those skilled in the art.

In one example, the program instructions 116 further cause the device 100 to provide for display, via the user interface 108, an indication to proceed with a delivery of the medicament 103 within the medicament container 101 to a patient if the determined volume of the medicament 103 within the medicament container 101 is less than a threshold difference from the expected volume of the medicament 103 within the medicament container 101. The threshold difference between the determined volume of the medicament 103 within the medicament container 101 and the expected volume of the medicament 103 within the medicament container 101 may be ±0.5%, ±1%, ±1.5%, ±2%, ±3%, ±4%, ±5%, ±6%, ±7%, ±8%, ±9%, or ±10%, as non-limiting examples.

In another example, the program instructions 116 further cause the device 100 to provide for display, via the user interface 108, an indication to stop or prohibit a dispense of the medicament 103 within the medicament container 101 to a patient if the determined volume of the medicament 103 within the medicament container 101 is greater than a threshold difference from the expected volume of the medicament 103 within the medicament container 101. The threshold difference between the determined volume of the medicament 103 within the medicament container 101 and the expected volume of the medicament 103 within the medicament container 101 may be ±0.5%±1%, ±1.5%, ±2%, ±3%, ±4%, ±5%, ±6%, ±7%, ±8%, ±9%, or ±10%, as non-limiting examples. This may particularly be relevant in case too little medicament 103 volume is present within the medicament container 101. For example, medicament dispense may be stopped or prohibited if the threshold difference is greater than −0.5% −1%, −1.5%, −2%, −3%, −4%, −5%, −6%, −7%, −8%, −9%, or −10%, as non-limiting examples. This means that less medicament 103 than expected is present in the medicament container 101.

In one example, the program instructions 116 further cause the device 100 to detect, based at least in part on the measured pressure, an air leak rate of the medicament container 101. In one example, the program instructions 116 further cause the device 100 to compare the detected air leak rate to a threshold value or acceptable/unacceptable "decay" rate. The device 100 may then provide a "go/no-go" indication to a dispensing or verifying pharmacist based on whether the measured leak rate is acceptable. In other words, the pharmacist may, informed by data from the indicated leak rate, choose to accept (i.e., dispense to a patient for later administration) or reject (i.e., do not dispense to a patient for later administration) the filled reservoir.

In one example, the program instructions 116 further cause the device 100 to write, via its communication interface 118, parameters associated with the medicaments intended delivery to the medicament container's communication interface 120. These parameters may include the measured medicament volume, the prescribed medicament volume, the prescribed delivery profile (e.g. delivery flow rate or pressure), and/or information about any sequential or paired medication dispensing, such as the number of medications in the combinatorial delivery, the types of medications in said delivery, the medicament's delivery "position" within the combinatorial delivery, and/or instructions relating to the risk profiles of the medications in the combinatorial delivery. These parameters may be pulled from an external device or system, such as an EHR, or may be entered manually on the volume-assessment device. The encoding of these parameters onto the medicament container's communication interface 120 may allow for the downstream communication of these parameters to a drug delivery device with its own communication interface.

In one example, the device 100 described above is provided in a preferred embodiment with an air pump, pressure sensor, battery, controller, readout, and activation button. It may optionally include an electronic or mechanical "vent" valve. The device 100 also has an interface point to the air side (internal sealed volume) of the medicament container 101. The device 100 may optionally also have a numeric display, target volume setpoint selector, NFC or RFID reader (for communicating with an RFID/NFC chip associated with the medicament container 101 and/or the rigid frame 105), and/or interface electronics for communicating with an EHR system with a wired and/or wireless connection.

FIGS. 4A-4D show an illustrative version of the device 100 being assembled onto the medicament container 101. The device 100 device is placed over the top of the medicament container 101, providing a pneumatic path from the pump to the air connection 122, and blocking the fluid outlet 124. As a result, when the cassette is pressurised, fluid is not expelled from the cassette, as it would be with a pneumatically-driven delivery device; this affordance also protects sterility of the medicament 103 contained within the medicament container 101 as the volume is probed. Optionally, in an alternative workflow, the HCP may "cap" the flexible medication container, preventing drug leakage in the presence of a pressurised medicament container 101. The medicament container 101 may also be provided with a check valve, filter, or other means to prevent air ingress into the filled medicament container 101 due to fluid movement and resulting suction.

Optionally, in an alternative embodiment, the device 100 does not contain an air pump; rather the known "quantity of air" could be injected via an operator action (e.g., depressing a button that displaces a passive piston).

As discussed above, the device 100, once assembled onto the medicament container 101, may be used to verify or measure the volume of medicament 103 contained in the medicament container 101. This figure may be simply measured by displaying the filled volume, or may be verified if there is a target setpoint selected on the device 100. This verification may optionally confirm that the measured volume is within pre-defined or locally defined accuracy or tolerance bounds, representing both measurement uncertainty as well as medication dosing tolerance (for instance, ±5% of nominal, or another suitable figure, based on the dispensing facility or characteristics of the medication to be administered as discussed above). Alternatively, volume may be verified by measuring it using the probe, and comparing it to the expected volume (e.g., an expected volume that is contained on a RFID/NFC chip associated with the medicament container 101 as a non-limiting example). The expected volume and/or its tolerance bounds may be configured by the device manufacturer, the drug manufacturer, the prescribing facility, the dispensing facility, and/or any operators representing those entities.

Figures 5A, 5B, 5C:
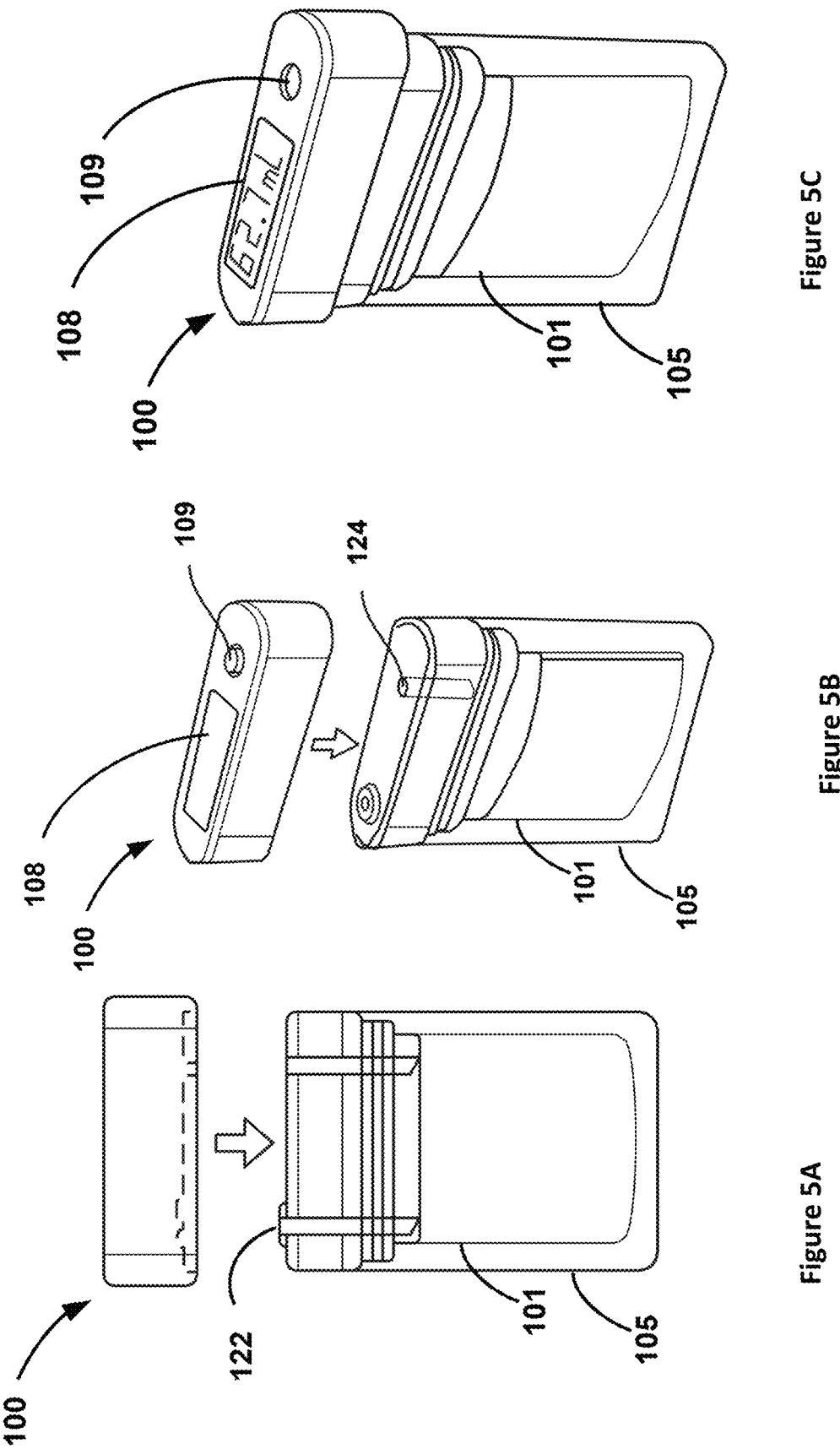
FIG. 5A illustrates a front view of another example device and an example medicament container, according to an example embodiment.
FIG. 5B illustrates a perspective view of the device and the medicament container of FIG. 5A, according to an example embodiment.
FIG. 5C illustrates a perspective view of the device and the medicament container of FIG. 5A with the device removably coupled to the medicament container, according to an example embodiment.

FIGS. 5A-5C are an alternative form embodiment of the device 100 of FIGS. 4A-4D. The device of FIG. 5A-5C is a top-reading view of the probed volume, which may be more ergonomic for workflow purposes, as multiple probed cassettes may be viewed side by side, which is particularly advantageous for verifying multiple medications in a regimen prior to dispensing.

Figure 6:
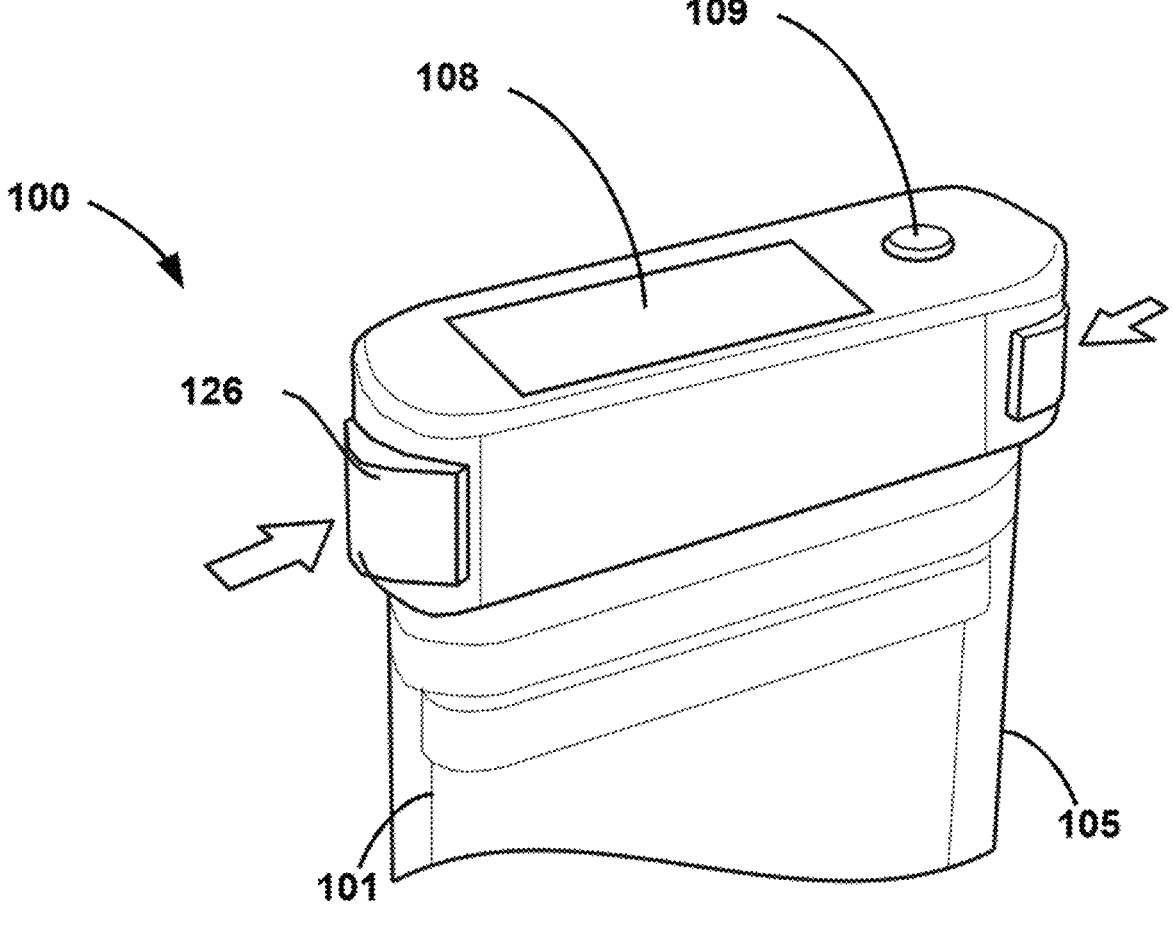
FIG. 6 illustrates a perspective view of another example device and an example medicament container, according to an example embodiment.

FIG. 6 shows an alternative removal method, whereby removal of the air pressure in the medicament container 101 happens passively when the release buttons 126 are pressed, which also releases the device 100 from the top connection with the medicament container 101.

As discussed above, some medications such as oncology regimens may be dispensed in sequences that should be administered in order as predefined by a physician. During dispensing of a medication regimen, it is ideal for the pharmacist to encode the sequence (or verify the sequence) during dispensing. It is also ideal for the pharmacist to encode the total number of medications within a sequence. Improved solutions in this area would enable the drug delivery device to enforce the proper administration sequence by an end user, preventing mis-ordered administration or incomplete administration of all medications.

In a first scenario, a set of cassettes is already provisioned with an ordinal sequence number. For instance, this may be done with stickers or clips containing a programmable RFID/NFC chip that are attached to each medicament container 101 during preparation by a pharmacist. Alternatively, this may be done by providing a programmable RFID/NFC chip in the medication cassette accessible to the apparatus described herein. In this scenario, the total number and order of medicament containers 101 is unknown a priori by the drug delivery system. Thus, the system needs to know a) that medicament container 101 are not duplicated (e.g., "1-2-3-4", not "1-2-2-4" or "1-1-3-4") and b) the total number of medicament container 101 in the sequence (1, 2, 3, . . . n).

In this scenario, during use of the device 100, the RFID/NFC chip is configured with the total number of cassettes, and the ordinal sequence of each cassette is verified as unique/unduplicated against the total expected number of cassettes in the sequence as the volume is probed. Further, the RFID/NFC chip is configured with the order of cassettes to detect a missing sequence (e.g., 1-3-4) where "2" is missing, or 1-2-4 where "3" is missing (and 4 should not be present).

In such an example, the program instructions 116 may further cause the device 100 to (i) set the total number of medications to be sequenced on the volume probe (e.g., via the selector switch or interface with an EHR system) corresponding to the total number of medications in the sequence as ordered by a physician, (ii) read the RFID/NFC chip associated with the medicament container 101 containing an ordinal sequence number, corresponding to the position of the medicament container 101 in the medication administration sequence as ordered by a physician, and verifying this number has not been duplicated (i.e., reused) during dispensing of the sequence, (iii) display an error to a user of the volume probe if a duplicated sequence number is determined during volume probe and/or RFID/NFC reading/writing, and/or (iv) in the case of a correct (i.e., valid) sequence position, program the RFID/NFC chip on the cassette with an integer corresponding to the total number of medications in the sequence as ordered by a physician.

In another example, the program instructions 116 may further cause the device 100 to display, via the user interface, an error message if one or more of (i) a duplicated sequence number is detected/determined, (ii) a missing sequence number is detected/determined, or (iii) an unexpected sequence number is detected/determined.

In a second scenario, a set of cassettes is provisioned with an RFID/NFC chip that is at least partially unprogrammed. The RFID/NFC chip may be partially programmed—for instance, with the drug name, rate, or volume—but is unprogrammed as to ordinal sequence number (i.e., position within a regimen/sequence) and/or total number of medications in the regimen/sequence.

In this second scenario, during use of the volume probe, the RFID/NFC chip is configured with the ordinal position of each cassette and total number of cassettes, both of which would be unknown a priori by the drug delivery system otherwise.

In such an example, the program instructions 116 may further cause the device 100 to (i) set the total number of medications to be sequenced on the device 100 (e.g., via the selector switch or interface with an EHR system) corresponding to the total number of medications in the sequence as ordered by a physician, (ii) program the RFID/NFC chip associated with the medicament container 101 with an ordinal sequence number, corresponding to the position of the medicament container 101 in the medication administration sequence as ordered by a physician, (iii) program the RFID/NFC chip associated with the medicament container 101 with an integer corresponding to the total number of medications in the sequence as ordered by a physician, and/or (iv) increment the sequence number after each volume probe and programming operation is successfully completed in preparation for the next volume probe and programming operation.

In another example, the program instructions 116 may further cause the device 100 to program the RFID/NFC chip associated with the medicament container 101 with one or more delivery instructions. These delivery instructions are then used by the device during delivery of the medicament. The one or more delivery instructions may include a flow rate setpoint, a pressure setpoint, an alarm volume, an indication of the types of errors to flag, an indication of the type of information to collect and transmit, sequence delay tolerances before an alarm, and a type of HER information to verify immediately ahead of dispense (such as in late-stage connectivity horizons), as non-limiting examples. Various examples use cases for the device 100 described above will now be described in additional detail. The examples are representative in nature and are no way exhaustive or limiting.

Cassette Leak Detection

While there are quality controls ensuring medicament container 101 robustness and critical-to-quality (CTQ) features in the manufacturing and assembling environments, there may be value in assessing that those CTQ features were not compromised in the interim secondary packaging, shipping, unboxing, or handling steps after the original medicament container 101 "checkout". As the device 100 contains means of pressurisation in addition to means of pressure sensing, an air leak rate could be determined by the device 100. The measured leak rate could be compared to reasonable bounds configured by the manufacturer or by appropriate standards (e.g., ISO, ASTM, USP, JP, or EP) to ensure the airtightness of the medicament container 101 has not been damaged or otherwise compromised before the dispensing of medication to the patient. In other words, the apparatus may be used for a variety of in-process quality control tests.

Verification of Dispensed Dose for Clinical Trials

In dose-finding clinical trials, the burden of the variable dosing may be placed on the dispensing pharmacist or pharmacy technician. The device 100 could add an unbiased dataset of "true" dispensed dose to the clinical trial administrator, as the volume measurements would not be "polluted" by operator biases and/or rounding errors. This dataset could be immensely valuable to determining optimal dose ranges and sensitivities, with a level of accuracy never before accessible in pharmacy-fill clinical trial phases. In a similar application, fill volumes may be reported in a clinical trial (e.g., the "pivotal" or Phase III study) and once the drug goes to market to contribute to post-market surveillance activities.

Calculation of Standard Fluid Volumes

In some instances, it may be preferable to flex medication concentration and instead fix the volume within the medicament container 101. In these instances, the device 100 may be used to identify the volume of medicament 103 in a medicament container 101, and then also be configured to calculate the volume to be added to "top up" ("QS" in pharmacy parlance) the fluid volume to a predetermined setpoint, usually with a diluent, as follows:

1. Set the device 100 to desired fixed volume (either by RFID/NFC chip reading with the cassette full volume, or by setting the volume probe manually)
2. Probe the volume of medicament 103 in the medicament container 101, as previously described
3. Calculate the difference between the max medicament container 101 volume and probed volume
4. Optionally, rounding the difference to correspond to the minimum dose scale on a syringe being used to add the QS diluent
5. Display the resulting amount to a user of the device 100
6. Optionally, re-probe the cassette to verify the correct QS amount has been added Referring to the above steps, table 2 describes the method steps using exemplary volumetric values.

202-208. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 200 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 202, the method 200 includes injecting, via a device 100 removably coupled to the medicament container 101, a known (first) quantity of fluid into a known volume surrounding the medicament container 101. As discussed above, in one example the fluid is a compressible fluid. At block 204, the method 200 includes measuring, via at least one pressure sensor 106 of the device 100, a pressure within the known volume surrounding the medicament container 101. At block 206, the method 200 includes determining, at least in part based on the measured pressure, a volume of a medicament 103 within the medicament container 101. At block 208, the method 200 includes providing for display (i.e., displaying), via a user interface 108, an indication of the volume of the medicament 103 within the medicament container 101.

By injecting the first quantity of fluid, a medicament 103 may be expelled from the medicament container 101 (medicament bag), which may also be referred to as medicament 103 injection or injection of the medicament 103.

TABLE 2

| Volume Probe Result (undiluted medicament, step 2) | Desired Final Fixed Volume (set by verifying HCP step 1) | Calculated "QS" to Add to reach fixed volume (displayed on volume probe, step 5) | Optional Display of QS volume to add (displayed on volume probe, based on step 4) |
| --- | --- | --- | --- |
| 37.5 mL | 50 mL | 12.5 mL | 13 mL* |
| 82.7 mL | 100 mL | 17.3 mL | 17 mL* |

*examples assume 20 mL syringe with 1 mL minimum scale increments

FIG. 7 is a block diagram of an example method 200, according to an example embodiment. Method 200 shown in FIG. 7 presents an embodiment of a method that could be used by the device 100 as described in FIGS. 3-6, as examples. Method 200 may include one or more operations, functions, or actions as illustrated by one or more of blocks In one example, the method 200 further includes removing fluid from the known volume surrounding the medicament container 101 to return the known volume surrounding the medicament container 101 to atmospheric pressure.

In another example, the method 200 further includes (i) receiving, via the user interface 108, an indication of an expected volume of the medicament 103 within the medicament container 101, and (ii) comparing the determined volume of the medicament 103 within the medicament container 101 with the expected volume of the medicament 103 within the medicament container 101. In one example, the indication of the expected volume of the medicament 103 within the medicament container 101 is received via a user input at the user interface 108. In another example, the indication of the expected volume of the medicament 103 within the medicament container 101 is received via a second communication interface 120 associated with the medicament container 101. In one example, the communication interface associated with the medicament container comprises a near-field communication (NFC) or radio frequency identification (RFID) tag.

In another example, the method 200 further includes providing for display, via the user interface, an indication to proceed with a delivery of the medicament 103 within the medicament container to a patient if the determined volume of the medicament 103 within the medicament container 101 is less than a threshold difference from the expected volume of the medicament 103 within the medicament container 101.

In another example, the method 200 further includes providing for display, via the user interface, an indication to stop a delivery of the medicament 103 within the medicament container 101 to a patient if the determined volume of the medicament 103 within the medicament container 101 is greater than a threshold difference from the expected volume of the medicament 103 within the medicament container 101.

In another example, the method 200 further includes preventing a dispense of the medicament 103 within the medicament container 101 to a patient if the determined volume of the medicament 103 within the medicament container 101 is greater than or less than a threshold difference from the expected volume of the medicament 103 within the medicament container 101. In one such example, preventing a dispense of the medicament 103 within the medicament container 101 to a patient comprises programming, via a communication interface associated with the medicament container 101, an indication that medicament container 101 is unsafe for use. Such an example provides a stopgap if a pharmacy were to accidentally dispense a medicament container 101 that "failed" testing with the probe.

In another example, the method 200 further includes enabling a delivery of the medicament 103 with the medicament container 101 to a patient if the determined volume of the medicament 103 within the medicament container 101 is less than a threshold difference from the expected volume of the medicament 103 within the medicament container 101.

In another example, the method 200 further includes programming, via the communication interface 120 associated with the medicament container 101, an indication that the determined volume of the medicament 103 within the medicament container 101 is less than a threshold difference from the expected volume of the medicament 103 within the medicament container 101.

In another example, the method 200 further includes providing for display, via the user interface 108, a difference between the determined volume of the medicament 103 within the medicament container 101 and the expected volume of the medicament 103 within the medicament container 101.

In another example, the method 200 further includes adding an amount of a diluent to the medicament container 101, wherein the amount of the diluent corresponds to the difference between the determined volume of the medicament 103 within the medicament container 101 and the expected volume of the medicament 103 within the medicament container 101.

By introducing a fluid into the known volume, the medicament 103 contained in the medicament container 101 may be expelled, i.e., injected into a patient (see above).

In another example, the method 200 further includes (i) after injection of the medicament 103 via the device 100, injecting a second known quantity of fluid into the known volume surrounding the medicament container 101, (ii) measuring, via the at least one pressure sensor 106 of the device 100, a second pressure within the known volume surrounding the medicament container 101, (iii) determining, at least in part based on the measured pressure, a final volume of the medicament 103 within the medicament container 101, and (iv) comparing the determined volume of the medicament 103 within the medicament container 101 with the final volume of the medicament 103 within the medicament container 101.

In another example, the method 200 further includes providing for display, via the user interface 108, an indication of the final volume of the medicament 103 within the medicament container 101.

In another example, the method 200 further includes programming, via a communication interface 120 associated with the medicament container 101, a record that the medicament container 101 is not empty after injection of the medicament 103 via the device 100.

In another example, the method 200 further includes detecting, based at least in part on the measured pressure, an air leak rate of the medicament container 101. In another example, the method 200 further includes programming, via a communication interface 120 associated with the medicament container 101, an indication that the determined air leak rate is greater than a threshold difference from an acceptable air leak rate. In another example, the method 200 further includes preventing a dispense of the medicament 103 within the medicament container 101 to a patient if the determined air leak rate is greater than a threshold difference from an acceptable air leak rate.

Medicament Container Disposal Example

The guidelines for safe management of healthcare waste are currently skewed towards landfilling and incineration as the safest options for most of the waste types generated. Some medicament containers 101, in normal use, are fully delivered to a patient, and thus are empty at the end of use. However, there may be instances where full delivery is not possible. For instance, medication delivery may be interrupted due to needle pullout, premature liftoff of the needle, or an adverse event, such as an infusion reaction.

Because the process of identifying which containers do and do not have medication is laborious, all used containers go into incineration to maximise safety. However, it would be useful to distinguish medicament containers that are completely empty from those that are partially full without a time-intensive or error prone process. Improved methods to distinguish these states could be used to shunt certain post-use containers to more sustainable recycling streams. For example, completely empty containers could be separated and reclaimed/recycled, while partially full containers could be properly incinerated.

As more advanced drug delivery devices become commonplace, there is information about the state of full drug delivery already present that can be advantageously used to improve this situation and divert empty containers into appropriate recycling or reclamation streams, reducing the total volume of waste incinerated.

Thus, in one example, the medicament container 101 may be programmed with medication status after administration, based on progress of drug administration with a drug delivery device. This information may be used (e.g., by scanning the used cassette) to distinguish full and empty cassettes after use and return. Users may then treat cassettes differently in terms of recycling/incineration based on the amount of medication they contain (e.g., shunting to recycling or reclamation in case of empty or partially full post-use reservoir, respectively).

In use, an airtight cassette of fixed volume is provided with an internally constrained flexible mediation container as previously described. The cassette (or other medicament container) is provided with an externally situated programmable RFID/NFC chip. The chip may be pre-configured (i.e., programmed) by pharmacy with certain information, such as the medication volume, flowrate, or sequence. The RFID/NFC chip may also be re-programmable, as described further below.

A drug delivery system is provided with a pneumatic drive interfacing with the sealed cassette. In addition, the drug delivery system contains RFID/NFC read/write capability, such as an RFID/NFC antenna and programmer. In other words, the drug delivery device can optionally read information from the cassette programmed during dispensing and write information onto the cassette during or after medication delivery using the apparatus.

Drug delivery may proceed in the following sequence:

1. Using the pneumatic drive, the cassette is probed at the beginning of the dispense. This starting value corresponds to the filled volume of the cassette (e.g., as filled by pharmacy prior to dispensing to the user).
2. Using the pneumatic drive, the medication is dispensed. As the dispense progresses, the volume is tracked (decrementing the full volume).
3. At the conclusion of dispense (either end of dose or error condition), the dispensed volume is compared to the full volume; alternatively, the volume in the cassette may be re-probed.
4. If the dispensed volume is approximately equal to the full volume (subject to some predetermined threshold), the cassette is empty, with only minimal (trace) residual volume. The drive controller re-programs the RFID/NFC chip on the cassette as empty.
5. If the dispensed volume is less than the full volume (subject to some predetermined threshold), the cassette contains meaningful residual medication. The drive controller re-programs the RFID/NFC chip on the cassette as partially full.
6. Steps 1-5 are repeated if multiple medications are administered in sequence; otherwise, the method proceeds.
7. The user sends all the cassettes to the takeback center; the takeback center scans all NFC chips upon receipt.
8. Cassettes that scan as "empty" can have materials separated and recycled.
9. Cassettes that scan as "partially full" are sent for incineration, for proper disposal of residual medicament, per local regulations.
10. Optionally, scan data (full/partial doses) may be uploaded to a patient electronic health record or patient support program for further intervention (e.g., patient coaching, adherence intervention, replacement dose for partial administration.

Figure 8B:
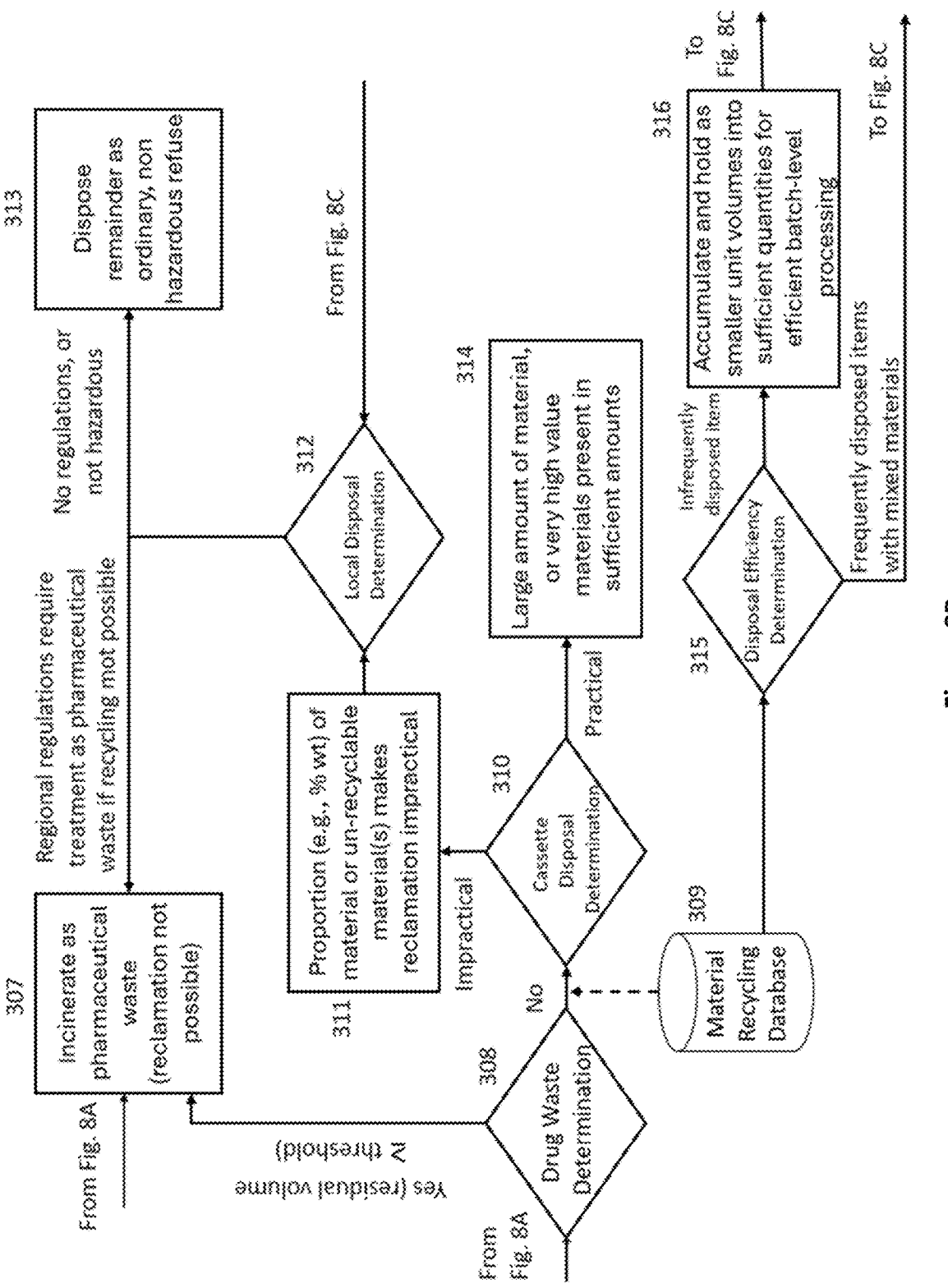
Figure 8C:
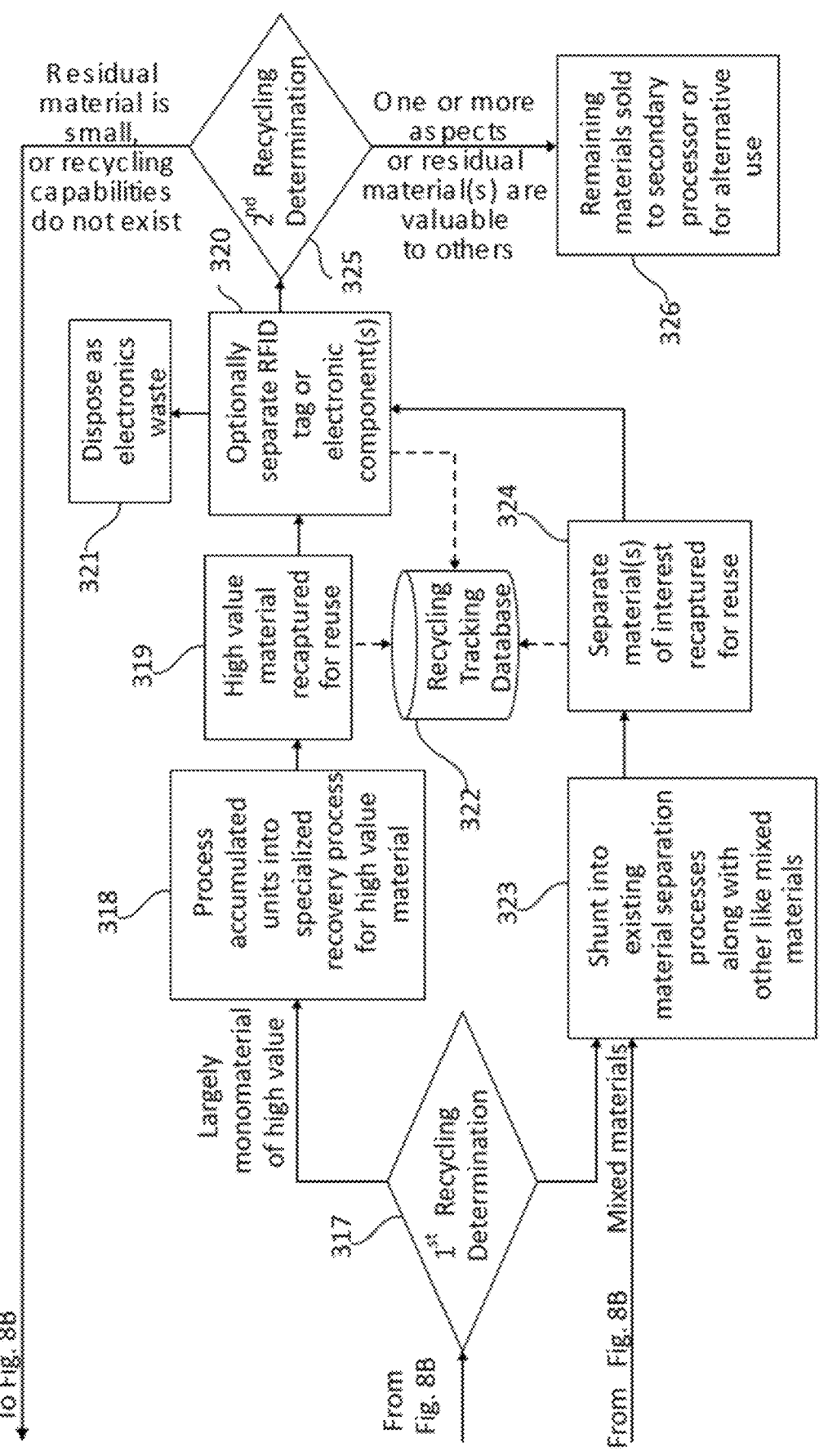

FIGS. 8A-8C shows a schematic drawing of a process to determine how to dispose of the device 100 after an injection is completed. As shown in FIG. 8A, the process may begin with block 301 with an interrogation of the cassette (e.g., device 100) to determine whether the cassette is part of a clinical trial. This step acts as a potential last ambush point to gather data post-administration from the cassette and to ensure all cassettes are returned (and potentially full doses administered). If it is determined that the cassette is part of a clinical trial, the process continues to block 302 with the cassette tags being read, and data is transferred into the clinical trial management system. The process then continues to block 303 where the cassette is received by a disposal facility (this may include intermediate processors and/or sorters). Block 303 could be done through a mail back process, by emptying out a sharps collector with multiple devices in it, or some other process. If it is determined that the cassette is not part of a clinical trial, the process moves directly to block 303.

The process continues at block 304 with a compatibility determination of the cassette to determine if the cassette includes the necessary disposal information. If a determination is made that there is an RFID tag (or other communication interface associated with the device) that is readable, the process continues at block 305 with reading the cassette RFID tag to collection post-administration information. In one example, the post-administration information includes one or more of a drug name or type, a volume of remaining medication, a container size, and regional information (such as a location of the device). The process may also include access to a drug disposal database 306. The drug disposal database 306 may include one or more threshold values (i.e., what is "empty"?) on general, drug-specific, regional level, or based on container size (e.g., % of max capacity remaining), as non-limiting examples. In one example, this information may be provided on the RFID tag at the point of manufacture. If a determination is made that there is not an RFID tag (or other communication interface associated with the device) or that the RFID tag is unreadable, the process continues in FIG. 8B at block 307 with incinerating the device as pharmaceutical waste as reclamation is not possible.

The process continues at block 308 with a drug waste determination, specifically, whether or not a threshold volume of medicament is still present in the medicament container of the device after administration of the injection. If the residual volume of the medicament in the medicament container of the device is greater than or equal to a threshold value, the process continues at block 307 with incinerating the device as pharmaceutical waste as reclamation is not possible. The process may also include access to a material recycling database 309. The material recycling database 309 may contain information on materials of construction of the device, resin type/subtype identifier, weight or proportion of one or more materials, manufacturer, presence/absence of electronic components or batteries, other custom recycling information (similar to 1-6 recycling codes in US). In one example, this information may be provided on the RFID tag at the point of manufacture.

If the residual volume of the medicament in the medicament container of the device is less than a threshold value, the process continues at block 310 with a cassette disposal determination. Specifically, at block 310 a determination is made whether or not it is practical to recycle the device based on one or more factors. If a determination is made that recycling of the device is impractical (e.g., at block 311 a proportion (e.g., % wt) of materials or un-recyclable material(s) makes reclamation impractical), the process continues to block 312 for a local disposal determination. The location disposal determination at block 312 takes into consideration the requirements of regional disposal regulations. If a determination is made that regional regulations require treatment of the device as pharmaceutical waste if recycling is not possible, then the process continues at block 307 with incinerating the device as pharmaceutical waste as reclamation is not possible. Conversely, if a determination is made that regional regulations allow treatment of the empty device as nonhazardous, the process continues at block 313 with disposing the remainder of the device as ordinary, nonhazardous refuse.

If, at block 310, a determination is made that recycling of the device is practical (e.g., at block 314 a determination is made that a large amount of material, or very high value materials are present in sufficient amounts in the device), the process continues to block 315 with a disposal efficiency determination. If a determination is made that the device is made up of an infrequently disposed item, the process continues at block 316 with accumulate and hold as smaller unit volumes accumulate into sufficient quantities for efficient batch-level processing. The process then continues in FIG. 8C with a first recycling determination at block 317. If a determination is made at block 317 that the device is largely monomaterial of high value, the process continues at block 318 with processing accumulated units into specialised recovery process for high value material. This captures the scenario where we have a cassette of largely single material (lots of one material). The process continues at block 319 with the high value material recaptured for reuse. This might focus on a single material of interest, or several. This branch is really about separating lots of a very expensive material. It may be possible that other materials could be left behind (e.g., stainless steel needles) or be shunted to secondary recovery (in this stream or by others). The process continues at block 320 with optionally separating the RFID tag or electronic component(s). The process continues at block 321 with disposing the RFID tag or electronic component(s) as electronics waste. The process may include a recycling tracking database 322, which may be used to track recycling activity over time. The recycling tracking database 322 may further be useful to support "net zero" claims or to support government credits/incentives.

If a determination is made at block 315 that the device is made up of (a) frequently disposed item(s) and/or with mixed materials, the process continues in FIG. 8C at block 323 with shunting into existing material separation processes along with other like mixed materials. If there is a lot of these materials consistently, this stream reduces down to continuous take-in-and-recycle, replacing the stockpile until a batch approach is appropriate. The shunting at block 323 could include a variety of separation techniques. For instance, it is possible to grind everything then separate with magnets for stainless steel components, by density or vibration for rubber/plastic/glass, etc. The separation techniques are exemplary only and are discussed for illustrative purposes only.

If a determination is made at block 317 that the device is made up of mixed materials, the process continues at block 323 with shunting into existing material separation processes along with other similar mixed materials. Strategically, this is aimed at segregating waste (e.g., pens in one bin, cassettes in another, etc.) until a "batchable" mass is reached, which can then be reclaimed in one shot. This is one way of provisioning for a high unit volume in the future while still being cost effective to recycle at lower (initial) volumes. Put another way, efficiency may be preserved as high volume is available on a "continuous" basis. The process continues at block 324 with separating material(s) of interest to be recaptured for reuse. The process continues at block 320 with optionally separating the RFID tag or electronic component(s). The process continues at block 321 with disposing the RFID tag or electronic component(s) as electronics waste.

The process further continues from block 320 with a second recycling determination at block 325. If a determination is made at block 325 that any residual material is small or that any further recycling capabilities do not exist, the process continues to block 312 of FIG. 8B for a local disposal determination. If a determination is made that regional regulations require treatment of the device as pharmaceutical waste if recycling is not possible, then the process continues at block 307 with incinerating the device as pharmaceutical waste as reclamation is not possible. Conversely, if a determination is made that regional regulations allow treatment of the empty device as nonhazardous, the process continues at block 313 with disposing the remainder of the device as ordinary, nonhazardous refuse. If a determination is made at block 325 that one or more aspects of residual material(s) are valuable to others, the process continues at block 326 with the selling the remaining materials to a secondary processor or otherwise for alternative use.

FIG. 9 is a block diagram of an example method 400, according to an example embodiment. Method 400 shown in FIG. 9 presents an embodiment of a method that could be used by the device 100 as described in FIGS. 3-6, as examples. Method 400 may include one or more operations, functions, or actions as illustrated by one or more of blocks 402-408. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 400 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 402, the method 400 includes, after injection of a medicament 103 via a device 100, determining a volume of the medicament 103 within a medicament container 101 of the device 100. At block 404, the method includes programming, via a communication interface 118 associated with the medicament container, an indication of one or more disposal parameters of the device 100 based at least in part on the determined volume of the medicament 103 within the medicament container 101 of the device 100.

In one example, the one or more disposal parameters comprise a record indicating whether (i) the medicament container 101 is empty or (ii) the medicament container 101 is not empty after injection of the medicament 103 via the device 100.

In another example, the one or more disposal parameters comprise a record indicating (i) the medicament container 101 should be recycled if a determination is made that the medicament container 101 is empty after injection of the medicament via the device 100 or (ii) the medicament container 101 should not be recycled if a determination is made that the medicament container 101 is not empty after injection of the medicament 103 via the device 100. In one example, the one or more disposal parameters comprise a record indicating the medicament container 101 should be incinerated or otherwise destroyed if a determination is made that the medicament container 101 is not empty after injection of the medicament 103 via the device 100.

In another example, the one or more disposal parameters comprise a record of a threshold residual volume associated with whether the medicament container 101 is empty or not empty after injection of the medicament 103 via the device 100.

In another example, the record of threshold residual volume is used as a comparator to determine whether the medicament container 101 is empty or not empty after injection of the medicament 103 via the device 100.

In another example, the one or more disposal parameters comprise an indication of one or more recycling and/or material processing steps based on a determination of one or more materials that make up the medicament container 101.

In another example, the method 400 further includes segregating, via the communication interface, a medicament container 101 for one or more recycling or material processing steps.

In another example, the one or more disposal parameters comprise an indication of one or more materials that make up the medicament container 101, as discussed in additional detail above. In another example, the one or more disposal parameters comprise an indication of a location of the medicament container 101. Such information may be used to associate one or more local disposal requirements with the one or more disposal parameters to ensure that disposal of the medicament container 101 complies with local regulations.

In another example, the communication interface associated with the medicament container comprises a near-field communication (NFC) or radio frequency identification (RFID) tag, as discussed in additional detail above.

In another example, the method 400 further includes transmitting, via the communication interface 118, the indication of one or more disposal parameters of the device 100 to an external device.

It will be appreciated that other arrangements are possible as well, including some arrangements that involve more or fewer steps than those described above, or steps in a different order than those described above.

According to a further embodiment which will be described with reference to FIG. 10, a medication cassette/ medicament bag, in particular a vial-filled medication cassette, with drive parameter programming is provided.

Medications may be compounded-prepared in an aseptic manner—by a pharmacy pr physician from vials or other bulk storage containers, such as vials. These medications are manipulated to accommodate fixed dosing, weight-based dosing, or body surface area dosing using syringes, needles, and vial spikes. Additionally, medications may be compounded even if the dose is not variable (i.e., "fixed" or "flat" dosing") if a filled vial is the only presentation available (i.e., a prefilled reservoir, such as a flexible bag, is not available), as is in the case of some biologic medications and frequently, investigational medications used in clinical trials.

As outlined above, currently, a pharmacist or pharmacy technician prepares a given medicament compound (e.g., a predefined amount of an oncology medication) and places it in a final container, such as a syringe, IV bag, or medication cassette. This workflow is common for IV medications, but increasingly, for subcutaneous (SC) medications, such as those delivered with a manual syringe. This embodiment is directed towards providing a quick and efficient vial filled configuration, and allowing to use an automated delivery device (either as an alternative to manual medicament delivery in a clinic, or to enable at-home delivery by the patient themselves).

Ideally, these medications would retain the flexibility of IV compounding processes, while from an end user perspective have the simplicity of a prefilled container. Thus, there is a need for improvements to allow medications in vials to be better used with advanced drug delivery systems, and particularly, to better control medication delivery parameters of these systems.

Cassette-level control may be also desirable in clinical trials of a single investigational medication. In these studies, it is common to adjust the dosing parameters of a specific formulation based on participant randomisation. These are a formalised part of clinical development. Dose escalation studies are used in early clinical trials (e.g., Phase 1/2) to establish the recommended dose of new drugs or drug combinations; the goal is to avoid exposing too many patients to subtherapeutic doses while preserving safety (i.e., due to overexposure). These study designs define a starting dose as the level of the drug at a certain volume (e.g., mg/mL). Then, a dose increment is defined, corresponding to the increased or decreased dose relative to the starting dose, each increment corresponding to a change in dose. These so-called "up-and-down" trial designs are common in oncology, aimed at escalating or de-escalating the dose with diminishing fractions of the preceding dose depending on the absence or presence of severe toxicity in the previous cohort of treated patients. These designs may also be guided by measurements of pharmacokinetic parameters, known as the pharmacologically guided dose escalation (PGDE) method. Thus, there are needs for improvements to accommodate consistent delivery with minimal configuration or programming of a multitude of clinical trial conditions with a single device.

In addition, clinical trials are necessarily run with a single medication, but in the case of oncology, trials are often run with multiple medications. These can include an investigational medication, either in combination with other investigational medication(s) or approved medication(s). Moreover, each of these medications may be dosed differently, either based on the disease state, cancer subtype, or other factors. Thus, there is an need for improved apparatus and methods to deliver multiple medications, all with different parameters and customise a single drug for different administration conditions, especially in oncology.

In some configurations, a prefilled cassette may have a preprogrammed tag with all drug parameters. Such a tag or chip may be read by a drug delivery device (e.g., by antenna or passive excitation) and carries parameters associated with one or more aspects of the drug delivery for that medication container. However, this is not always possible, in particular for flexible medicament bags, and the presented configuration works with a vial specifically designed for SC administration.

Figure 10A:
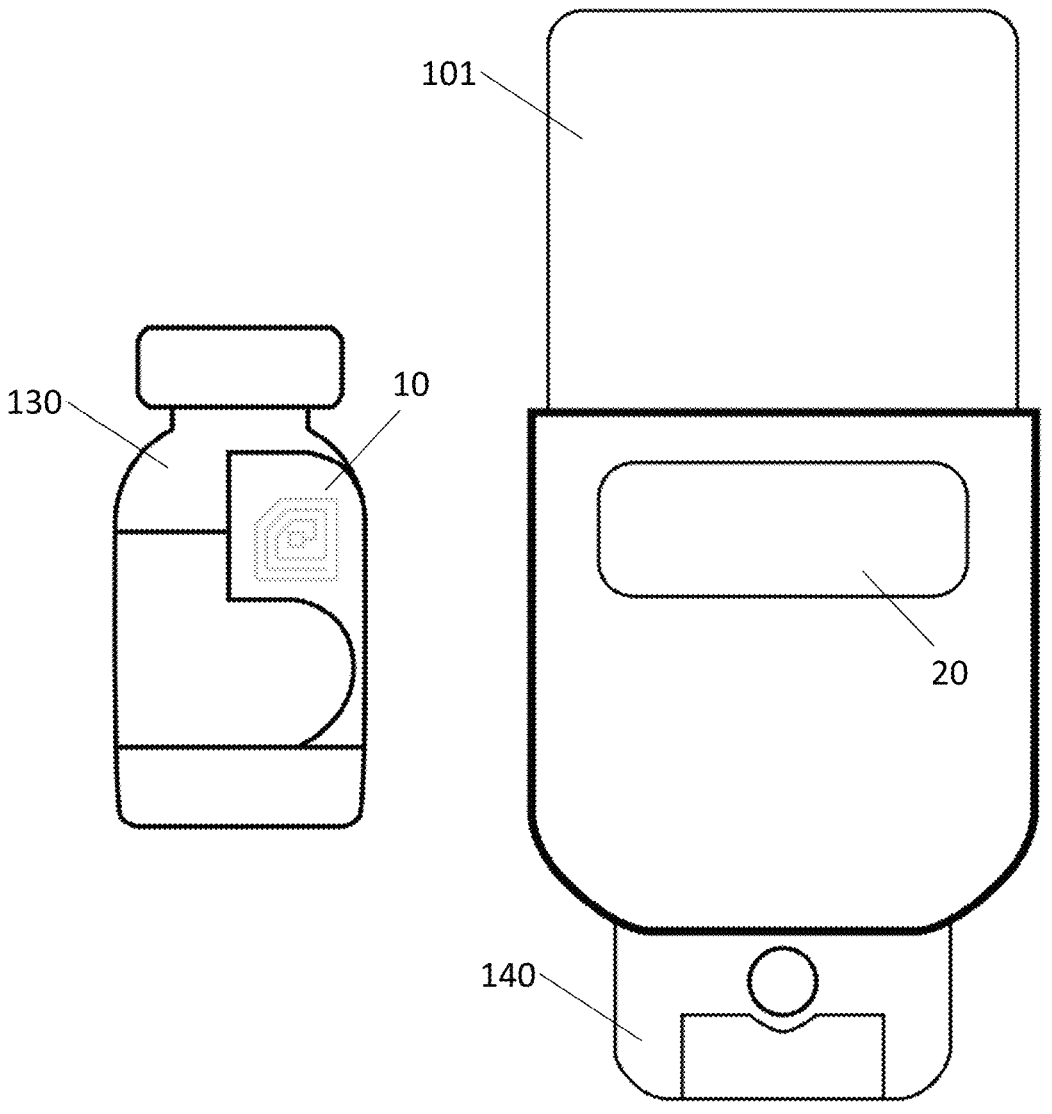
FIGS. 10A and 10B are schematic depictions of an example embodiment.

FIG. 10A shows a schematic depiction of a medicament bag/container 101 and a vial 130 (bottle, container) containing a medicament to be filled into the medicament container 101. The vial 130 In FIG. 10A comprises a tag 10 which is removably provided on an outer surface of the vial 130. The Medicament container 101 is further depicted with a filling port 140 for filling the medicament container 101 (e.g., via a Luer connection).

Thus, the vial 130 is configured with a tag 10 (as described above, e.g., an RFID tag) that is designed to cooperate with a reusable delivery device or drive unit. The tag 10 may be configured with delivery parameters such as, by way of example, cassette expiration date (stability), medication UDI/identifier/serial/lot, filling site/machine/equipment ID, actual filled volume, or flow rate (mL/min). Other parameters mentioned throughout the specification or suitable in the field of medicament delivery may also be used. These parameters may be specific to the medication itself.

Further, different parameters may be provided for different medications.

The tag 10 may be embedded in the drug label, which is removable from the vial 130. The label may be provided in several layers or a perforated section to allow retention of other drug information (e.g., as required by regulatory authorities).

As outlined above and with reference to FIG. 10A, an illustrative medicament container 101 is configured with a removable pharmacy filling tool (in that case a port 140). The filling tool 140 may also be omitted as the container 101 may be filled by other methods.

The cassette or medicament container 101 may be provided without any tag, and simply a target area 20, or may be supplied with a pre-configured RFID tag (not shown). The target area 20 may ensure that a tag 10 or label is placed on a region of the medicament container 101 which allows reading the information on the tag 10 by a drive device or the like.

The cooperating delivery device, as a failsafe, may be configured to ignore cassettes without a readable tag. This would improve safety, as this indicates that no delivery parameters are present.

Also, a preconfigured tag, for example, may be provided on the medicament container 101 and may correspond to that of a pharmacy-filled cassette. The container may be supplied from the manufacturer with an RFID tag and parameters corresponding to comparatively less granular control over flow (versus a prefilled cassette), operating in "empty all" mode at a set operating pressure or target flow rate, without regard to fluidic characteristics or medication specific parameters.

Figure 10B:
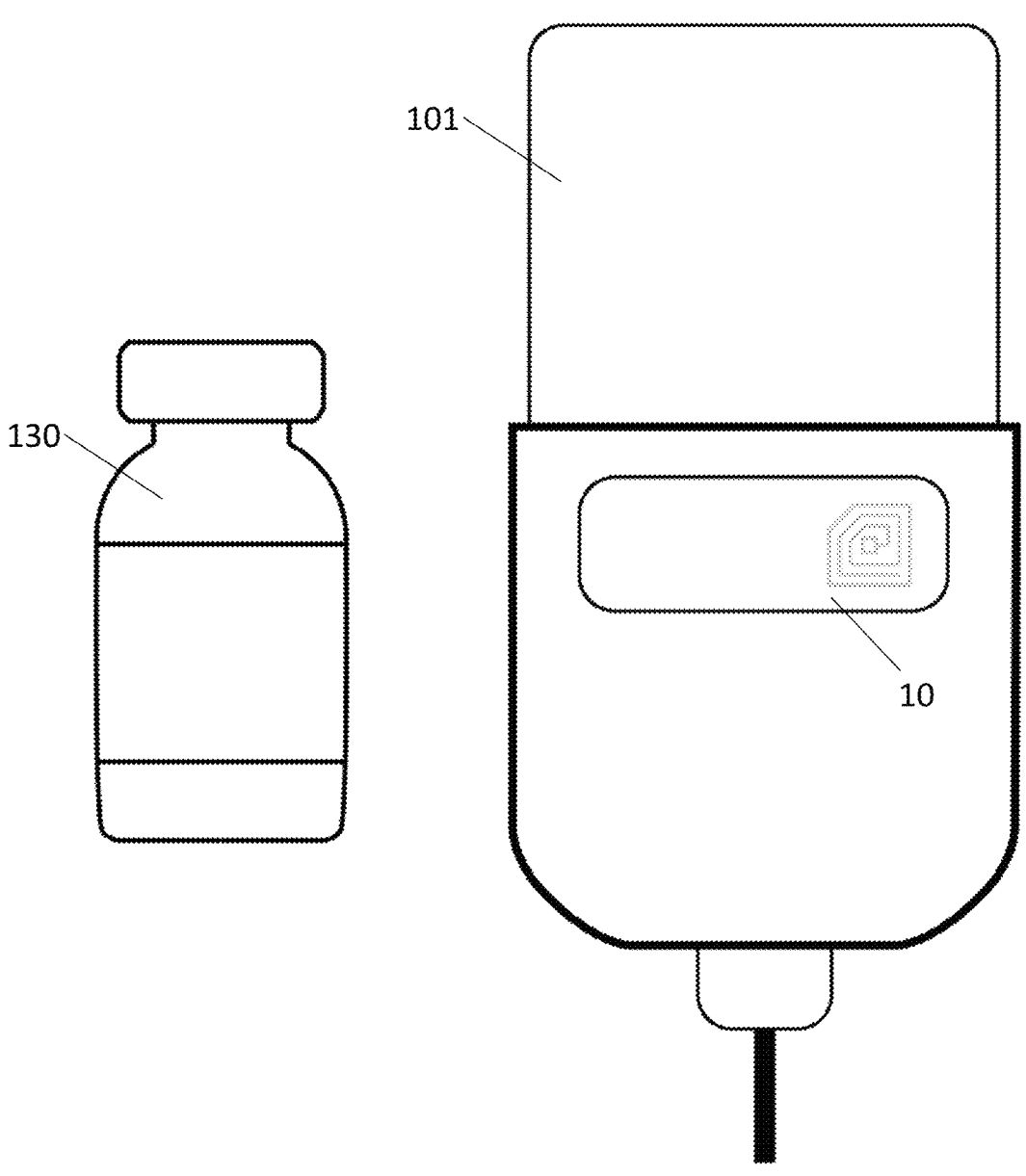

After filling the content of the vial 130 into the medicament container 101, the tag 10 may be removed from the vial and placed on the medicament container 101, in particular on the target area 20. This is shown in FIG. 10B.

In other words, the user filling the device (e.g., a pharmacist or pharmacy technician) peels the label/sticker/tag 10 from the empty (or partially empty) vial 130 and applies it to the target area 20 on the medicament container 101. The tag 10 may obscure a sticker (or other indicia) initially provided on the medicament container 101, in particular on the target area 10.

The resulting configuration of a medicament container 101 with the tag 10 originally provided on the vial 130 placed thereon may then be inserted into a delivery device, which follows the "recipe", i.e., the instructions and/or parameters, on the applied RFID 10 to administer the medication of the vial 130 (now in the medicament container 101). The medicament container 101 may be compliant with reusable devices which administer the medicament according to the information provided on the tag 10.

This concept may be expanded for use in multi-medication delivery, or for use in clinical trials. For example, the medicament container 101 with the tag 10 placed thereon may be combined with one approved medication provided in another container and another clinical trial medication provided in a further container. These containers may then be administered in sequence, as prescribed by the clinical trial, by sequentially inserting them into the drive, administering each, removing the empty cassette, and repeating the process until all three cassettes are delivered. The sequence and parameters for medicament delivery may be stored on respective tags provided on each cassette.

The present embodiment may also be used to override existing information contained on a medicament container 101 with a pre-existing (RFID) tag.

For example, the vial 130 label or tag 10 may be provided with an RFID-blocking material adjacent to the adhesive layer, configured to block RFID signals (i.e., reading the tag below) when applied over the pre-existing tag. This may be done by providing the vial label 10 with a layer of metal foil (or other suitable material) prior to applying the adhesive. Such a material may be flexible enough to conform to the vial 130 circumference and to be easily removed by a user, but resilient enough to remain intact when applied to the medicament container 101 as described previously. The label 10 may also be intentionally oversized to the required size, so as to provide additional coverage over a pre-existing tag if a user slightly misaligns the vial label when applying it to itself.

By blocking the RFID in an underlying tag from being read, this allows superseding instructions to be provided to a delivery device via the over-labelled tag, effectively "reprogramming" a medicament container/cassette 101 without actually changing it.

Further, in an embodiment, a clinical trial cassette/medicament container 101 may be provided with a filling tool, allowing the medicament container 101 to be filled with a syringe. This medicament container 101 may be either provided with an existing RFID tag (e.g., pharmacy-filled configuration) or may be provided with no tag during initial manufacturing (see above).

The medicament container 101 may be filled from a vial 130 with a fixed concentration and volume of medication, and the vial 130 may be equipped with the tag 10 described herein, e.g., corresponding to a specific trial condition (delivered volume, rate, etc.). Applying this tag 10 to the medicament container 101 either overrides the existing medicament container 101 programming (if a tag is present), or provides it (if no tag is present). This allows empty medicament containers 101 to be filled at a clinical trial site just prior to use, from a familiar container using familiar processes, and for clinical trial supply processes to be unchanged. In this manner, a single cassette/container/bag design can be provided to administer multiple delivery conditions of a single investigational or approved medication consistently without individual programming steps, even across multiple clinical trial sites.

In summary, the present disclosure also encompasses a system comprising a vial and a medicament container. The medicament container comprises a target area, the vial comprises a readable and programmable tag removably provided on an outer surface thereof, the tag comprising a plurality of parameters of the medicament container in the medicament container and the tag is configured to be removed from the vial and placed on the target area.

As outlined throughout the specification, the tag may comprise a quick response (QR) code, a near field communication (NFC) tag or a radio frequency identification (RFID) tag. The NFC tag or RFID tag may be pre-programmed. The parameters may comprise, e.g., at least one of a medicament name, an initial medicament volume, a residual medicament volume, a prescription dose, a time of manufacture, a time of filling, a dispensing sequence, medication information, pharmacy information, physician information, portable app information, or user instructions.

The target area may also comprise an RFID tag. The tag may comprise a blocking layer configured to block reading and programming of the target area's RFID tag when the tag is placed on the target area.

Thus, the above-described target area 20 for labelling cassette improves the safety of medicament delivery, as it allows a drug delivery device to read an RFID tag 10 and thus ensure that the correct parameters are used or prevent medicament delivery in case no tag 10 is found. Also, the drive device may be configured to deliver a medicament using default parameters for any cassette 101 without a tag 10.

The tag 10 removed from the vial 130 and applied to the medicament container 101 can populate, supplement or override delivery parameters when applied to the medicament container 101.

Therefor, a blocker or "override" layer may be provided in the tag to cover an existing RFID sticker with programming information, thus providing a superseding or "reprogramming" functionality.

Hence, a faster path to provide a control system functionality without changing the primary container is provided.

The simplified configuration allows a single cassette design to administer multiple delivery conditions of a single (e.g., investigational or approved) medication Further, this allows use of an IV-concentration mAb to be used for SC delivery without re-formulation, and with a full workflow fit (backwards compatibility) to existing IV workflows (as the tag is invisible to an IV workflow).

The embodiments described herein, unless indicated otherwise, may be combined with each other. All embodiments described herein can be used for a device for measuring a medicament container containing medicament for the treatment and/or prophylaxis of one or more of many different types of disorders. Exemplary disorders include, but are not limited to: rheumatoid arthritis, inflammatory bowel diseases (e.g. Crohn's disease and ulcerative colitis), hypercholesterolaemia, diabetes (e.g. type 2 diabetes), psoriasis, migraines, multiple sclerosis, anaemia, lupus, atopic dermatitis, asthma, nasal polyps, acute hypoglycaemia, obesity, anaphylaxis and allergies. Exemplary types of medicaments that could be included in the medicament delivery devices described herein include, but are not limited to, small molecules, hormones, cytokines, blood products, antibodies, antibody-drug conjugates, bispecific antibodies, proteins, fusion proteins, peptibodies, polypeptides, pegylated proteins, protein fragments, protein analogues, protein variants, protein precursors, chimeric antigen receptor T cell therapies, cell or gene therapies, oncolytic viruses, or immunotherapies and/or protein derivatives. Exemplary medicaments that could be included in the medicament delivery devices described herein include, but are not limited to (with non-limiting examples of relevant disorders in brackets): etanercept (rheumatoid arthritis, inflammatory bowel diseases (e.g. Crohn's disease and ulcerative colitis)), evolocumab (hypercholesterolaemia), exenatide (type 2 diabetes), secukinumab (psoriasis), erenumab (migraines), alirocumab (rheumatoid arthritis), methotrexate (amethopterin) (rheumatoid arthritis), tocilizumab (rheumatoid arthritis), interferon beta-1a (multiple sclerosis), sumatriptan (migraines), adalimumab (rheumatoid arthritis), darbepoetin alfa (anaemia), belimumab (lupus), peginterferon beta-1a' (multiple sclerosis), sarilumab (rheumatoid arthritis), semaglutide (type 2 diabetes, obesity), dupilumab (atopic dermatitis, asthma, nasal polyps, allergies), glucagon (acute hypoglycaemia), epinephrine (anaphylaxis), insulin (diabetes), atropine and vedolizumab (inflammatory bowel diseases (e.g. Crohn's disease and ulcerative colitis)), ipilimumab, nivolumab, pembrolizumab, atezolizumab, durvalumab, avelumab, cemiplimab, rituximab, trastuzumab, ado-trastuzumab emtansine, fam-trastuzumab deruxtecan-nxki, pertuzumab, transtuzumab-pertuzumab, alemtuzumab, belantamab mafodotin-blmf, bevacizumab, blinatumomab, brentuximab vedotin, cetuximab, daratumumab, elotuzumab, gemtuzumab ozogamicin, 90-Yttrium-ibritumomab tiuxetan, isatuximab, mogamulizumab, moxetumomab pasudotox, obinutuzumab, ofatumumab, olaratumab, panitumumab, polatuzumab vedotin, ramucirumab, sacituzumab govitecan, tafasitamab, or margetuximab. Pharmaceutical formulations including, but not limited to, any drug described herein are also contemplated for use in the medicament delivery devices described herein, for example pharmaceutical formulations comprising a drug as listed herein (or a pharmaceutically acceptable salt of the drug) and a pharmaceutically acceptable carrier. Pharmaceutical formulations comprising a drug as listed herein (or a pharmaceutically acceptable salt of the drug) may include one or more other active ingredients, or may be the only active ingredient present.

Exemplary medicaments that could be included in the medicament delivery devices described herein include, but are not limited to, an immuno-oncology or bio-oncology medications such as immune checkpoints, cytokines, chemokines, clusters of differentiation, interleukins, integrins, growth factors, enzymes, signaling proteins, pro-apoptotic proteins, anti-apoptotic proteins, T-cell receptors, B-cell receptors, or costimulatory proteins.

Exemplary medicaments that could be included in the medicament delivery devices described herein include, but are not limited to, those exhibiting a proposed mechanism of action, such as HER-2 receptor modulators, interleukin modulators, interferon modulators, CD38 modulators, CD22 modulators, CCR4 modulators, VEGF modulators, EGFR modulators, CD79b modulators, Trop-2 modulators, CD52 modulators, BCMA modulators, PDGFRA modulators, SLAMF7 modulators, PD-1/PD-L1 inhibitors/modulators, B-lymphocyte antigen CD19 inhibitors, B-lymphocyte antigen CD20 modulators, CD3 modulators, CTLA-4 inhibitors, TIM-3 modulators, VISTA modulators, INDO inhibitors, LAG3 (CD223) antagonists, CD276 antigen modulators, CD47 antagonists, CD30 modulators, CD73 modulators, CD66 modulators, CDw137 agonists, CD158 modulators, CD27 modulators, CD58 modulators, CD80 modulators, CD33 modulators, APRIL receptor modulators, HLA antigen modulators, EGFR modulators, B-lymphocyte cell adhesion molecule modulators, CDw123 modulators, Erbb2 tyrosine kinase receptor modulators, mesothelin modulators, HAVCR2 antagonists, NY-ESO-1 OX40 receptor agonist modulators, adenosine A2 receptors, ICOS modulators, CD40 modulators, TIL therapies, or TCR therapies.

Exemplary medicaments that could be included in the medicament delivery devices described herein include, but are not limited to, a multi-medication treatment regimen such as AC, Dose-Dense AC, TCH, GT, EC, TAC, TC, TCHP, CMF, FOLFOX, mFOLFOX6, mFOLFOX7, FOLF-CIS, CapeOx, FLOT, DCF, FOLFIRI, FOLFIRINOX, FOLFOXIRI, IROX, CHOP, R-CHOP, RCHOP-21, Mini-CHOP, Maxi-CHOP, VR-CAP, Dose-Dense CHOP, EPOCH, Dose-Adjusted EPOCH, R-EPOCH, CODOX-M, IVAC, HyperCVAD, R-HyperCVAD, SC-EPOCH-RR, DHAP, ESHAP, GDP, ICE, MINE, CEPP, CDOP, GemOx, CEOP, CEPP, CHOEP, CHP, GCVP, DHAX, CALGB 8811, HIDAC, MOPAD, 7+3, 5+2, 7+4, MEC, CVP, RBAC500, DHA-Cis, DHA-Ca, DHA-Ox, RCVP, RCEPP, RCEOP, CMV, DDMVAC, GemFLP, ITP, VIDE, VDC, VAI, VDC-IE, MAP, PCV, FCR, FR, PCR, HDMP, OFAR, EMA/CO, EMA/EP, EP/EMA, TP/TE, BEP, TIP, VIP, TPEx, ABVD, BEACOPP, AVD, Mini-BEAM, IGEV, C-MOPP, GCD, GEMOX, CAV, DT-PACE, VTD-PACE, DCEP, ATG, VAC, VelP, OFF, GTX, CAV, AD, MAID, AIM, VAC-IE, ADOC, or PE.

Exemplary medicaments that could be included in the medicament delivery devices described herein include, but are not limited to, those used for chemotherapy, such as an alkylating agent, plant alkaloid, antitumor antibiotic, antimetabolite, or topoisomerase inhibitor, enzyme, retinoid, or corticosteroid. Exemplary chemotherapy medicaments include, by way of example but not limitation, 5-fluorouracil, cisplatin, carboplatin, oxaliplatin, doxorubicin, daunorubicin, idarubicin, epirubicin, paclitaxel, docetaxel, cyclophosphamide, ifosfamide, azacitidine, decitabine, bendamustine, bleomycin, bortezomib, busulfan, cabazitaxel, carmustine, cladribine, cytarabine, dacarbazine, etoposide, fludarabine, gemcitabine, irinotecan, leucovorin, melphalan, methotrexate, pemetrexed, mitomycin, mitoxantrone, temsirolimus, topotecan, valrubicin, vincristine, vinblastine, or vinorelbine.

While various aspects and embodiments have been disclosed herein, other aspects and embodiments will be apparent to those skilled in the art. All embodiments within and between different aspects of the devices and methods can be combined unless the context clearly dictates otherwise. The various aspects and embodiments disclosed herein are for purposes of illustration and are not intended to be limiting, with the true scope being indicated by the claims.

Some other aspects of the invention are described by the following clauses.

1. A device configured to be removably coupled to a medicament container, comprising:

a pump;

a battery configured to supply power to the pump;

at least one pressure sensor;

at least one memory storage element;

at least one processor; and data storage including program instructions stored thereon that when executed by the at least one processor, cause the device to:

inject, via the pump, a known quantity of fluid into a known volume surrounding the medicament container;

measure, via the pressure sensor, a pressure within the known volume surrounding the medicament container;

determine, at least in part based on the measured pressure, a volume of a medicament within the medicament container; and provide for display, via a user interface, an indication of the volume of the medicament within the medicament container.

2. The device of clause 1, wherein the program instructions further cause the device to:

remove fluid from the known volume surrounding the medicament container to return the known volume surrounding the medicament container to atmospheric pressure.

3. The device of any one of clauses 1-2, wherein the indication of the volume of the medicament within the medicament container comprises a numerical value.

4. The device of any one of clauses 1-3, wherein the program instructions further cause the device to:

transmit, via a communication interface, the volume of the medicament within the medicament container to an external device.

5. The device of any one of clauses 1-4, wherein the program instructions further cause the device to:

receive an indication of an expected volume of the medicament within the medicament container; and compare the determined volume of the medicament within the medicament container with the expected volume of the medicament within the medicament container.

6. The device of clause 5, wherein the indication of the expected volume of the medicament within the medicament container is received via a user input at the user interface.

7. The device of clause 5, wherein the indication of the expected volume of the medicament within the medicament container is received via a communication interface on a rigid frame at least partially surrounding the medicament container.

8. The device of clause 7, wherein the communication interface on the rigid frame comprises a near-field communication (NFC) or radio frequency identification (RFID) tag.

9. The device of any one of clauses 5-8, wherein the program instructions further cause the device to:

provide for display, via the user interface, an indication to proceed with a delivery of the medicament within the medicament container to a patient if the determined volume of the medicament within the medicament container is less than a threshold difference from the expected volume of the medicament within the medicament container.

10. The device of any one of clauses 5-8, wherein the program instructions further cause the device to:

provide for display, via the user interface, an indication to stop or prohibit a dispense of the medicament within the medicament container to a patient if the determined volume of the medicament within the medicament container is greater than or less than a threshold difference from the expected volume of the medicament within the medicament container.

11. The device of any one of clauses 1-10, wherein the program instructions further cause the device to:

detect, based at least in part on the measured pressure, an air leak rate of the medicament container.

12. The device of any one of clauses 1-11, wherein the program instructions further cause the device to:

determine, via a communication interface associated with the medicament container, an indication of an ordinal sequence number corresponding to a position of the medicament container in a medication administration sequence.

13. The device of clause 12, wherein the program instructions further cause the device to:

display, via the user interface, an error message if one or more of (i) a duplicated sequence number is detected, (ii) a missing sequence number is detected, or (iii) an unexpected sequence number is detected.

14. The device of any one of clauses 1-13, wherein the program instructions further cause the device to:

program, via a communication interface associated with the medicament container, one or more delivery instructions for the device.

15. A method comprising:

injecting, via a device removably coupled to a medicament container, a known quantity of fluid into a known volume surrounding the medicament container;

measuring, via at least one pressure sensor of the device, a first pressure within the known volume surrounding the medicament container;

determining, at least in part based on the measured first pressure, a volume of a medicament within the medicament container; and providing for display, via a user interface, an indication of the volume of the medicament within the medicament container.

16. The method of clause 15, further comprising:

removing fluid from the known volume surrounding the medicament container to return the known volume surrounding the medicament container to atmospheric pressure.

17. The method of any one of clauses 15-16, further comprising:

receiving, via the user interface, an indication of an expected volume of the medicament within the medicament container; and comparing the determined volume of the medicament within the medicament container with the expected volume of the medicament within the medicament container.

18. The method of clause 17, wherein the indication of the expected volume of the medicament within the medicament container is received via a user input at the user interface.

19. The method of clause 17, wherein the indication of the expected volume of the medicament within the medicament container is received via a communication interface associated with the medicament container.

20. The method of clause 19, wherein the communication interface associated with the medicament container comprises a near-field communication (NFC) or radio frequency identification (RFID) tag.

21. The method of any one of clauses 17-20, further comprising:

providing for display, via the user interface, an indication to proceed with a delivery of the medicament with the medicament container to a patient if the determined volume of the medicament within the medicament container is less than a threshold difference from the expected volume of the medicament within the medicament container.

22. The method of any one of clauses 17-21, further comprising:

providing for display, via the user interface, an indication to stop or prohibit a dispense of the medicament within the medicament container to a patient if the determined volume of the medicament within the medicament container is greater than or less than a threshold difference from the expected volume of the medicament within the medicament container.

23. The method of any one of clauses 17-22, further comprising:

programming, via the communication interface associated with the medicament container, an indication that the determined volume of the medicament within the medicament container is less than a threshold difference from the expected volume of the medicament within the medicament container.

24. The method of any one of clauses 17-23, further comprising:

providing for display, via the user interface, a difference between the determined volume of the medicament within the medicament container and the expected volume of the medicament within the medicament container.

25. The method of clause 24, further comprising:

adding an amount of a diluent to the medicament container, wherein the amount of the diluent corresponds to the difference between the determined volume of the medicament within the medicament container and the expected volume of the medicament within the medicament container.

26. The method of any one of clauses 16-25, further comprising:

after injection of the medicament via the device, injecting a second known quantity of fluid into the known volume surrounding the medicament container;

measuring, via the pressure sensor of the device, a second pressure within the known volume surrounding the medicament container;

determining, at least in part based on the measured second pressure, a final volume of the medicament within the medicament container; and comparing the determined volume of the medicament within the medicament container with the final volume of the medicament within the medicament container.

27. The method of clause 26, further comprising:

providing for display, via the user interface, an indication of the final volume of the medicament within the medicament container.

28. The method of any one of clauses 16-27, further comprising:

programming, via a communication interface associated with the medicament container, a record that the medicament container is not empty after injection of the medicament via the device.

29. The method of any one of clauses 16-28, further comprising:

detecting, based at least in part on the measured pressure, an air leak rate of the medicament container.

30. The method of clause 29, further comprising:

programming, via a communication interface associated with the medicament container, an indication that the determined air leak rate is greater than a threshold difference from an acceptable air leak rate.

31. The method of any one of clauses 29-30, further comprising:

preventing a dispense of the medicament within the medicament container to a patient if the determined air leak rate is greater than a threshold difference from an acceptable air leak rate.

32. The method of any one of clauses 16-31, further comprising:

preventing a dispense of the medicament within the medicament container to a patient if the determined volume of the medicament within the medicament container is greater than or less than a threshold difference from the expected volume of the medicament within the medicament container.

33. The method of clause 32, wherein preventing a dispense of the medicament comprises:

programming, via a communication interface associated with the medicament container, an indication that medicament container is unsafe for use.

34. The method of any one of clauses 16-33, further comprising:

enabling a delivery of the medicament with the medicament container to a patient if the determined volume of the medicament within the medicament container is less than a threshold difference from the expected volume of the medicament within the medicament container.

35. A method comprising:

after injection of a medicament via a device, determining a volume of the medicament within a medicament container of the device; and programming, via a communication interface associated with the medicament container, an indication of one or more disposal parameters of the device based at least in part on the determined volume of the medicament within the medicament container of the device.

36. The method of clause 35, wherein the one or more disposal parameters comprise a record indicating whether (i) the medicament container is empty or (ii) the medicament container is not empty after injection of the medicament via the device.

37. The method of any one of clauses 35-36, wherein the one or more disposal parameters comprise a record indicating (i) the medicament container should be recycled if a determination is made that the medicament container is empty after injection of the medicament via the device or (ii) the medicament container should not be recycled if a determination is made that the medicament container is not empty after injection of the medicament via the device.

38. The method of any one of clauses 35-37, wherein the one or more disposal parameters comprise a record of a threshold residual volume associated with whether the medicament container is empty or not empty after injection of the medicament via the device.

39. The method of clause 38, wherein the record of threshold residual volume is used as a comparator to determine whether the medicament container is empty or not empty after injection of the medicament via the device.

40. The method of any one of clauses 35-39, wherein the one or more disposal parameters comprise an indication of one or more materials that make up the medicament container.

41. The method of any one of clauses 35-40, wherein the one or more disposal parameters comprise an indication of one or more recycling and/or material processing steps based on a determination of one or more materials that make up the medicament container.

42. The method of any one of clauses 34-36, wherein the communication interface associated with the medicament container comprises a near-field communication (NFC) or radio frequency identification (RFID) tag.

43. The method of any one of clauses 34-37, further comprising:

transmitting, via the communication interface, the indication of one or more disposal parameters of the medicament container to an external device.

44. The method of any one of clauses 34-37, further comprising:

segregating, via the communication interface, a medicament container for one or more recycling or material processing steps.

45. The method of any one of clauses 34-38, wherein the one or more disposal parameters comprise an indication of a location of the medicament container.

46. System comprising a vial and a medicament container, wherein the medicament container comprises a target area;

wherein the vial comprises a readable and programmable tag removably provided on an outer surface thereof, the tag comprising a plurality of parameters of the medicament container in the medicament container; and wherein the tag is configured to be removed from the vial and placed on the target area.

47. System according to clause 46, wherein the tag comprises a quick response (QR) code, a near field communication (NFC) tag or a radio frequency identification (RFID) tag.

48. System according to clause 47, wherein the NFC tag or RFID tag is pre-programmed.

49. System according to any one of clauses 46-48, wherein the parameters comprise at least one of a medicament name, an initial medicament volume, a residual medicament volume, a prescription dose, a time of manufacture, a time of filling, a dispensing sequence, medication information, pharmacy information, physician information, portable app information, or user instructions.

50. System according to any one of clauses 46-49, wherein the target area comprises an RFID tag; and wherein the tag comprises a blocking layer configured to block reading and programming of the target area's RFID tag when the tag is placed on the target area.

The invention claimed is:

1. A method for configuring a medicament container, the method comprising:

filling a medicament container with a predetermined amount of a medicament, or obtaining a pre-filled medicament container;

obtaining, by a mobile terminal, a plurality of parameters of the medicament contained in the medicament container via a readable and programmable tag, wherein the parameters of the medicament comprise at least a volume, wherein the volume is determined by a pressure sensor, wherein the tag is provided on the medicament container, wherein the tag is multi-layered, comprising a first layer with a first set of parameters and a second layer with a second set of parameters, and wherein a removal of the first layer of the tag prevents the first set of parameters from being obtained and allows the second set of parameters to be obtained, and wherein the parameters are obtained via a portable app run on the mobile terminal;

displaying, on the mobile terminal, the parameters obtained via the tag; and configuring, via the portable app, at least one of the parameters of the medicament.

2. The method according to claim 1, wherein the portable app is downloaded to the mobile terminal according to the parameters obtained via the tag.

3. The method according to claim 1, wherein the tag comprises a quick response, QR, code, a near field communication, NFC, tag or a radio frequency identification, RFID, tag.

4. The method according to claim 3, wherein the NFC tag or RFID tag is pre-programmed.

5. The method according to claim 1, wherein the parameters comprise at least one of a medicament name, an initial medicament volume, a residual medicament volume, a prescription dose, a time of manufacture, a time of filling, a dispensing sequence, medication information, pharmacy information, physician information, portable app information, or user instructions.

6. The method according to claim 1, wherein the mobile terminal is a handheld mobile terminal.

7. The method according to claim 1, wherein the portable app is an Instant App or App Clip.

8. The method according to claim 1, wherein the tag is at least partially removable.

9. The method according to claim 1, wherein the first set of parameters comprises different information than the second set of parameters.

10. A medicament container comprising a readable and programmable tag, the medicament container being configured for use with the method according to claim 1.

11. A configurable drug dispensing system comprising:
  a medicament container comprising a readable and programmable tag; and
  a mobile terminal configured to perform the method according to claim 1.

12. The method according to claim 6, wherein the handheld mobile terminal is a smartphone.

\* \* \* \* \*